United States Patent
Relton et al.

(10) Patent No.: US 6,720,764 B2
(45) Date of Patent: Apr. 13, 2004

(54) MAGNETIC SENSOR SYSTEM USEFUL FOR DETECTING TOOL JOINTS IN A DOWNHOLE TUBING STRING

(75) Inventors: Mahendran S. Relton, Sugar Land, TX (US); John S. Burrington, Houston, TX (US); Jason P. MacInnis, Houston, TX (US); Jonathan J. Falcon, Broussard, LA (US)

(73) Assignee: Thomas Energy Services Inc., Lafayette, LA (US)

( * ) Notice: Subject to any disclaimer, the term of this patent is extended or adjusted under 35 U.S.C. 154(b) by 0 days.

(21) Appl. No.: 10/125,005

(22) Filed: Apr. 16, 2002

(65) Prior Publication Data

US 2003/0193329 A1 Oct. 16, 2003

(51) Int. Cl.[7] ............ G01B 7/00; G01N 27/42; G01V 3/00; E21B 47/09

(52) U.S. Cl. ............ 324/235; 324/228; 324/207.2; 324/207.21; 324/207.24; 324/262; 166/255.1; 166/66.5

(58) Field of Search ................ 324/219–221, 324/229, 232, 235, 239–243, 262, 207.2, 207.21, 207.24; 166/250.01, 66, 66.5, 255.1, 255.2

(56) References Cited

U.S. PATENT DOCUMENTS

| | | | |
|---|---|---|---|
| 3,056,920 A | 10/1962 | Herrald | |
| 3,103,976 A | 9/1963 | de Vries et al. | |
| 3,114,876 A | 12/1963 | Schuster | |
| 3,434,046 A | 3/1969 | Wilson et al. | |
| 3,570,594 A | 3/1971 | Hamilton | |
| 3,843,923 A | 10/1974 | de Vries et al. | |
| 3,881,375 A | 5/1975 | Kelly | |
| 3,882,377 A | 5/1975 | Kelly | |
| 3,883,797 A | 5/1975 | Abrukin | |
| 4,061,967 A | 12/1977 | Hall | |
| 4,110,688 A | 8/1978 | Bailey | |
| 4,202,490 A | 5/1980 | Gunkel et al. | |
| 4,328,704 A | 5/1982 | Arpasi et al. | |
| 4,422,041 A | 12/1983 | Lienau | |
| 4,439,730 A | * 3/1984 | Kauffman | 324/232 |
| 4,578,642 A | 3/1986 | Moake et al. | |
| 4,578,991 A | 4/1986 | Nowlin | |
| 4,629,991 A | 12/1986 | Wheeler | |
| 4,636,727 A | 1/1987 | Kahil et al. | |
| 4,698,631 A | 10/1987 | Kelly, Jr. et al. | |
| 4,710,712 A | 12/1987 | Bradfield et al. | |
| 4,715,442 A | 12/1987 | Kahil et al. | |
| 4,792,756 A | 12/1988 | Lam et al. | |
| 4,808,925 A | 2/1989 | Baird | |
| 4,964,462 A | 10/1990 | Smith | |
| 5,014,781 A | 5/1991 | Smith | |
| 5,142,128 A | 8/1992 | Perkin et al. | |
| 5,202,680 A | 4/1993 | Savage | |
| 5,323,856 A | 6/1994 | Davis et al. | |

(List continued on next page.)

FOREIGN PATENT DOCUMENTS

| EP | 0412535 A1 | 2/1991 |
|---|---|---|
| GB | 1602065 | 11/1981 |

*Primary Examiner*—Gerard R. Strecker
(74) *Attorney, Agent, or Firm*—Vinson & Elkins L.L.P.

(57) ABSTRACT

A method and apparatus for detecting ferrous changes passing axially through a cylindrical space. In one embodiment, the method comprises surrounding the cylindrical space with a nonmagnetic cylinder having an outer wall and a cylindrical axis; creating an alternating magnetic field in the cylindrical space, the magnetic field created by a rotatable permanent magnet; monitoring the magnetic field with magnetic flux sensors placed outside the outer walls; and detecting changes in the magnetic field as ferrous matter passes axially through the cylindrical space. In other embodiments, the apparatus identifies ferrous changes as the tool joints that connect a jointed tubing string as the tubing string is moved in or out of a well bore, or as the presence or absence of a coiled tubing string in the well bore.

71 Claims, 10 Drawing Sheets

U.S. PATENT DOCUMENTS

| | | | |
|---|---|---|---|
| 5,360,967 A | 11/1994 | Perkin et al. | |
| 5,361,838 A | 11/1994 | Kilgore | |
| 5,429,190 A | 7/1995 | Kilgore et al. | |
| 5,532,589 A | 7/1996 | Gammell | |
| 5,626,192 A | 5/1997 | Connell et al. | |
| 5,720,345 A | 2/1998 | Price et al. | |
| 5,750,896 A | 5/1998 | Morgan et al. | |
| 5,963,033 A | * 10/1999 | Booker | 324/240 |
| 6,003,597 A | 12/1999 | Newman | |
| 6,032,739 A | 3/2000 | Newman | |
| 6,253,842 B1 | 7/2001 | Connell et al. | |
| 6,304,078 B1 | 10/2001 | Jarrard et al. | |
| 6,346,806 B1 | 2/2002 | Schabuble et al. | |
| 6,356,076 B1 | 3/2002 | Luetzow | |
| 6,366,085 B1 | 4/2002 | Yeshurun et al. | |
| 6,411,084 B1 | 6/2002 | Yoo | |
| 6,448,760 B1 | 9/2002 | Neumann et al. | |
| 6,492,808 B1 | 12/2002 | Sukhorukov et al. | |
| 6,515,474 B1 | 2/2003 | Dielschneider et al. | |
| 6,541,966 B1 | 4/2003 | Keene | |
| 6,552,532 B1 | 4/2003 | Sako | |
| 6,556,005 B1 | 4/2003 | Oomkes | |
| 6,573,709 B1 | 6/2003 | Gandel et al. | |
| 6,577,123 B2 | 6/2003 | Schroeder et al. | |
| 6,584,846 B2 | 7/2003 | Wesselak | |
| 6,586,929 B1 | 7/2003 | Luetzow | |

* cited by examiner

MAGNETIC SENSOR SYSTEM USEFUL FOR DETECTING TOOL JOINTS IN A DOWNHOLE TUBING STRING

BACKGROUND OF THE INVENTION

In oil and gas wells, jointed pipes are conventionally inserted and stripped from a well bore under pressure. The intermittent sections that comprise the jointed pipes are typically connected by tool joints, which are generally threaded end connections.

In standard operations, the jointed pipes are moved in or out of the well bore through blow out preventers (BOPs). The mounting and operation of BOPs are well known in the art. Typically, two BOPs are mounted on a spool (a "BOP spool"), with one BOP at the upper end of the spool and the other BOP at the lower end of the spool. The BOPs operate to separate the high pressure of the well bore from atmospheric pressure. Each BOP comprises a hydraulic ram that seals around the outside diameter of the pipe to pressure seal the well bore. The upper ram is normally kept closed when a pipe is stripped from the well. Because the BOP rams seal around the outside diameter of the piping, any reasonable increase in size of the piping may damage the rams and piping and may also compromise the sealing capabilities of the rams.

As a tool joint enters the bottom of the spool during stripping, the upper ram is closed, and the lower ram is open. When the tool joint clears the lower ram, the stripping of the pipe is temporarily suspended. The lower ram is then closed, and the spool is depressurized to atmospheric pressure. After depressurization, the upper ram is opened, and the stripping of the piping is resumed until the tool joint exits the upper BOP ram. The upper ram is then closed, and the spool is re-pressurized to the pressure of the well bore. After re-pressurization, the lower ram is opened, and the procedure is repeated upon entry of the next tool joint into the bottom of the spool. When jointed pipe is moved into the well instead of stripped from the well, the same procedures apply in clearing the tool joints of the BOPs but in the opposite order.

The movement of the tool joints through BOP spools is known to present operational problems. The rig operator is generally unable to see the tool joint enter the BOP spool. When a tool joint enters the BOP spool, if the operator does not stop the movement of the tool joint and properly open the closed BOP ram, the tool joint may contact the closed BOP ram, which may cause damage to the tool joint or BOP. If the damage is serious, the rig safety may be compromised, and a well blowout could occur. To prevent this occurrence, rig operators have historically estimated pipe lengths, and have then tallied pipe lengths between the joints to facilitate location of each tool joint as it enters the BOP spool. Errors in calculations or by the operator may cause the tool joint to strike a closed BOP ram. Further drawbacks of this process include the lack of speed at which the operator must work to prevent any such slight errors that may damage the BOP ram or tool joint.

In addition to jointed pipes, coiled tubing strings are conventionally inserted and stripped from a well bore under pressure, which also presents operational problems. In standard operations, the coiled tubing string is typically moved in or out of the well bore through a crown valve and a BOP stack. The crown valve is generally the top valve on the arrangement of pipes, valves and instruments typically found at the surface of a well bore, known colloquially as the "Christmas tree." The BOP stack may have a plurality of BOPs comprising at least one stripping BOP, which is different than the upper and lower BOP configuration that is standard for the jointed pipe operations.

As the coiled tubing string is stripped from the well bore, the crown valve is open and the stripping BOPs are closed. When the last of the coiled tubing string exits the crown valve and begins to enter the BOP stack, the crown valve must be closed to maintain the well pressure. If the crown valve is not closed, the well would be open to the atmosphere and thereby increase safety and environmental risks and exposures. To prevent this occurrence, historically a friction counter will be used to estimate the coiled tubing string length. Coil tubing personnel will mechanically operate the crown valve by carefully attempting to close the crown valve to identify when the coiled tubing string exits the crown valve. Errors in calculations by the friction counter and by the coil tubing personnel may result in flooding of the well. Further drawbacks also include the lack of speed at which the operator must work to prevent any such slight errors that may cause safety and environmental exposures.

Therefore, it is highly advantageous to correctly locate tool joints in the BOP spool and to correctly locate the last of the coiled tubing string to exit the crown valve. It will be understood that the presence of a pipe (for example a coiled tubing string) in a spool will cause a deviation in a magnetic field exerted across the spool. Because tool joints have larger outside diameter and mass than the pipe, the tool joints cause an even greater deviation in the magnetic field. Consequently, magnetic locators have been used in the past to identify the location of the tool joints and the presence of the coiled tubing string. For instance, magnetic sensors such as gradiometers have been used to identify the presence of tool joints in the BOP spool by sensing a change in the earth's magnetic field due to the presence of a tool joint. Problems encountered with this technology include interference from surrounding ferrous objects that may lead to false joint identification. Further, in deployments near the equator, it will be appreciated that readings of the earth's magnetic field tend towards zero, making it extremely difficult for magnetic sensors to identify the magnetic flux change due to the presence of a tool joint or the last of a coiled tubing string.

Besides identifying changes in the earth's magnetic field to locate a tool joint or identify the presence of a coiled tubing string, the prior art has also utilized electromagnets to identify piping. One such device is disclosed in U.S. Pat. No. 4,964,462. In the disclosure of this patent, a magnetic field is created by electromagnets attached to a nonmagnetic BOP spool that separates upper and lower BOPs. Sensors mounted on the nonmagnetic spool identify changes in the electromagnetic field that signify the presence of a tool joint. Improvements need to be made on using electromagnets in a well bore, whose operation requires potentially unsafe voltages and currents to be deployed down hole.

Consequently, there is a need for an improved method for inserting and stripping jointed pipes and coiled tubing strings from a well bore. Further, there is a need for a more safe and effective way of identifying tool joints in a BOP spool and identifying the presence of a coiled tubing string in a spool.

SUMMARY OF THE INVENTION

These and other needs in the art are addressed in one embodiment by an inventive method for detecting ferrous changes passing axially through a cylindrical space. The method comprises surrounding the cylindrical space with a nonmagnetic cylinder having an outer wall and a cylindrical axis; creating an alternating magnetic field in the cylindrical space, the magnetic field created by a rotatable permanent magnet; monitoring the magnetic field with magnetic flux sensors placed outside the outer walls; and detecting changes in the magnetic field as ferrous matter passes axially through the cylindrical space.

In another embodiment, the invention comprises an apparatus that identifies ferrous changes as a tool joint in a jointed tubing string with the tubing string moving in and out of a well bore and a plurality of the tool joints connecting sections of the jointed tubing string. The apparatus comprises a nonmagnetic cylindrical spool having a cylindrical axis, the tubing string and tool joints disposed to move axially in or out of the nonmagnetic cylindrical spool; and a sensor device attached to the nonmagnetic cylindrical spool, the sensor device having a source piece and at least one sensor piece, the source piece comprising a permanent magnet, the permanent magnet operatively rotatable.

In a third embodiment, the invention provides a method of identifying ferrous changes as a plurality of the tool joints connecting a jointed tubing string move in and out of a well bore, the method comprising: (a) moving a tubing string in or out of a well bore; (b) causing the tubing string to pass through a nonmagnetic cylindrical spool; (c) creating an alternating magnetic field across the nonmagnetic cylindrical spool; (d) sensing a deviation in the alternating magnetic field; and (e) identifying the deviation in the alternating magnetic field.

In a fourth embodiment, the invention provides a method of identifying ferrous changes while moving a jointed tubing string in and out of a well bore, a plurality of tool joints connecting the jointed tubing string, the method comprising: (a) moving the tubing string through an upper BOP, a lower BOP, and a nonmagnetic cylindrical spool; (b) separating the upper BOP and the lower BOP with the nonmagnetic cylindrical spool; (c) creating an alternating magnetic field across the nonmagnetic cylindrical spool; (d) sensing a deviation in the alternating magnetic field; (e) identifying the deviation in the alternating magnetic field; and (f) moving the tubing string in or out of the well bore without the tool joint contacting the upper BOP and the lower BOP.

According to a fifth embodiment, the invention provides an apparatus for identifying ferrous changes in a jointed tubing string, a plurality of tool joints connecting the jointed tubing string, the tubing string moving in and out of a well bore, the apparatus comprising a nonmagnetic cylindrical spool, an upper BOP, and a lower BOP, the tubing string moving in or out of the well bore through the nonmagnetic cylindrical spool, the upper BOP, and the lower BOP; the nonmagnetic cylindrical spool separating the upper BOP and the lower BOP; the upper BOP closable around the tubing string to form a pressure lock; the lower BOP closable around the tubing string to form a pressure lock; a rotatable permanent magnet attached to the nonmagnetic cylindrical spool, the permanent magnet rotatable about an axis substantially orthogonal to the cylindrical axis of the nonmagnetic cylindrical spool; a motor secured to the nonmagnetic cylindrical spool, the motor disposed to rotate the permanent magnet; a source field shaper secured to the nonmagnetic cylindrical spool, the source field shaper disposed to shape the magnetic field created by the rotating permanent magnet; at least two sensors secured to the nonmagnetic cylindrical spool, the sensors disposed to identify changes in the magnetic field; the sensors further disposed to create a processor-readable signal that identifies the change in the magnetic field; at least one sensor field shaper attached to the nonmagnetic cylindrical spool, the sensor field shaper disposed to shield the sensors from outside magnetic interference; the upper BOP openable to allow passage of the tool joint; and the lower BOP openable to allow passage of the tool joint.

In a sixth embodiment, the invention comprises an apparatus that identifies ferrous changes as a coiled tubing string moves in and out of a well bore. The apparatus comprises a nonmagnetic cylindrical spool having a cylindrical axis, the coiled tubing string disposed to move in and out of the nonmagnetic cylindrical spool along the cylindrical axis; and a sensor device attached to the nonmagnetic cylindrical spool, the sensor device having a source piece and at least one sensor piece, the source piece comprising a permanent magnet, the permanent magnet operatively rotatable.

In a seventh embodiment, the invention provides a method of identifying ferrous changes as a coiled tubing string moves in and out of a well bore, the method comprising: (a) moving a coiled tubing string in and out of a well bore; (b) causing the coiled tubing string to pass through a nonmagnetic cylindrical spool; (c) creating an alternating magnetic field across the nonmagnetic cylindrical spool; (d) sensing a deviation in the alternating magnetic field; and (e) identifying the deviation in the alternating magnetic field.

It will therefore be seen that a technical advantage of the invention includes a permanent magnet, thereby eliminating problems encountered by using the earth's magnetic field or by electromagnetic fields to identify changes in pipe diameter and/or mass. For instance, problems encountered with using the earth's magnetic field such as interference by surrounding ferrous objects is overcome. In addition, the magnetic reading of the present invention does not near zero at the equator, which overcomes another problem in detecting magnetic flux associated with using the earth's magnetic field. The present invention does not employ potentially unsafe voltages and currents down hole as does the use of an electromagnet. Further advantages include the rotatable permanent magnet minimizing interference from any residual magnetism of the pipe. In addition, a further technical advantage includes prevention of outside magnetic interference, which allows for identification of the ferrous changes. The invention also allows the tool joints to pass through a BOP spool without damaging the tubing string or the BOPs, which maintains the integrity of the well. In addition, the invention also allows a coiled tubing string to be inserted or stripped from a well while decreasing safety and environmental exposure risks.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
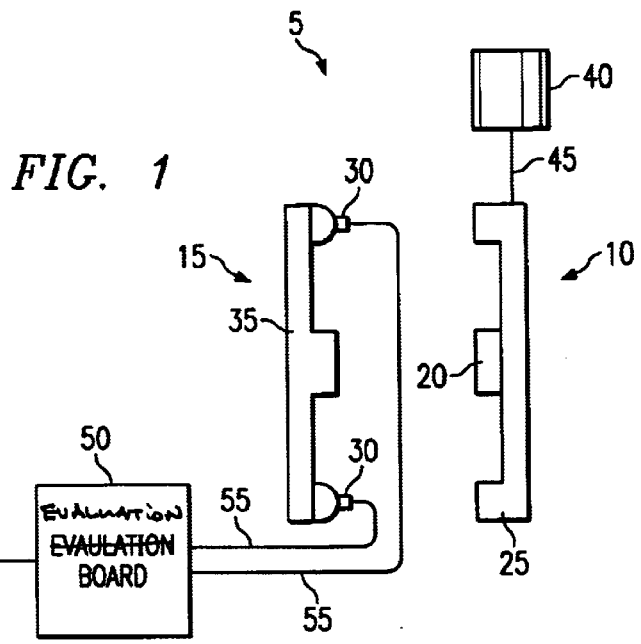
FIG. 1 illustrates one embodiment of a tool joint locator apparatus.

A first embodiment of the invention is described with respect to FIG. 1, in which a sensor device 5 comprises a source piece 10 and a sensor piece 15. The source piece 10 has a permanent magnet 20 and a source field shaper 25. The source field shaper 25 comprises a non-corrosive, soft magnetically permeable material, such as iron. Because the permanent magnet 20 exerts a magnetic field in all directions, the source field shaper 25 directs the magnetic field in the horizontal direction away from the source field shaper 25. As shown, the sensor piece 15 comprises sensors 30 and a sensor field shaper 35. The sensor field shaper 35 also comprises a non-corrosive, soft magnetically permeable material, again such as iron. The sensor field shaper 35 shields the sensors 30 from the effects of external magnetic fields such as the earth's magnetic field. A motor 40 is attached to the source piece 10 by a shaft 45.

In the embodiment illustrated in FIG. 1, the source piece 10 is advantageously E-shaped, with three separate horizontal sections and a vertical section. The center horizontal section is the permanent magnet 20. The upper and lower horizontal sections and the vertical section comprise the source field shaper 25. The source piece 10 is horizontally rotatable 360 degrees by the motor 40 and shaft 45. The shaft 45 that connects the motor 40 to the source piece 10 is embedded into the vertical section of the source piece 10 and runs lengthwise down the vertical section. The motor 40 horizontally rotates the source piece 10 about the vertical axis of the shaft 45, thereby creating the alternating magnetic field.

With further reference to FIG. 1, the sensor piece 15 is also advantageously E-shaped, with three separate horizontal sections and a vertical section. The upper and lower horizontal sections contain the sensors 30. The vertical section and the three horizontal sections comprise the sensor field shaper 35. A variety of sensor technologies known in the art may be used for the sensors 30 but preferably Hall effect sensors are used. Hall effect sensors are well known in the art. Examples of available Hall effect sensors include Honeywell SS 495A and Micronas HAL800 sensors. In the alternative, Anisotropic Magnetoresistive sensors or Giant Magnetoresistive sensors could be used for sensor technology instead of Hall effect devices. The center horizontal section serves as a return for the magnetic field, which helps shape the magnetic field. In addition to containing the sensors 30, the upper and lower horizontal sections also serve as conduit points for the return of the magnetic field thereby further helping shape the magnetic field.

The invention is not limited to an E-shaped sensor piece 15 as illustrated on FIG. 1. In another embodiment of the invention (not illustrated), the sensor field shaper 35 may have a vertical section and upper and lower horizontal sections but without a center horizontal section. In a further embodiment, the sensor piece 15 is separated into an upper and lower section, each section advantageously U-shaped and comprising a sensor field shaper 35 and a sensor 30. The sensor field shaper 35 of the upper section of the sensor piece 15 has a vertical section and upper and lower horizontal sections, with either the upper or lower horizontal sections containing the sensor 30. Alternatively, both the upper and lower horizontal sections may contain a sensor 30. The sensor field shaper 35 of the lower section of the sensor piece 15 also has a vertical section and upper and lower horizontal sections, with either the upper or lower horizontal sections containing the sensor 30. Alternatively, both the upper and lower horizontal sections may contain a sensor 30.

As further illustrated on FIG. 1, an evaluation board 50 is connected to the sensors 30 by evaluation board connectors 55. The evaluation board 50 comprises an analog to digital converter. Examples of available analog to digital converters include the Analog Devices AD7730 converter. A battery box 60 is connected to the evaluation board 50. Examples of available battery boxes 60 include the Orga Type CCA battery box.

Figure 2:
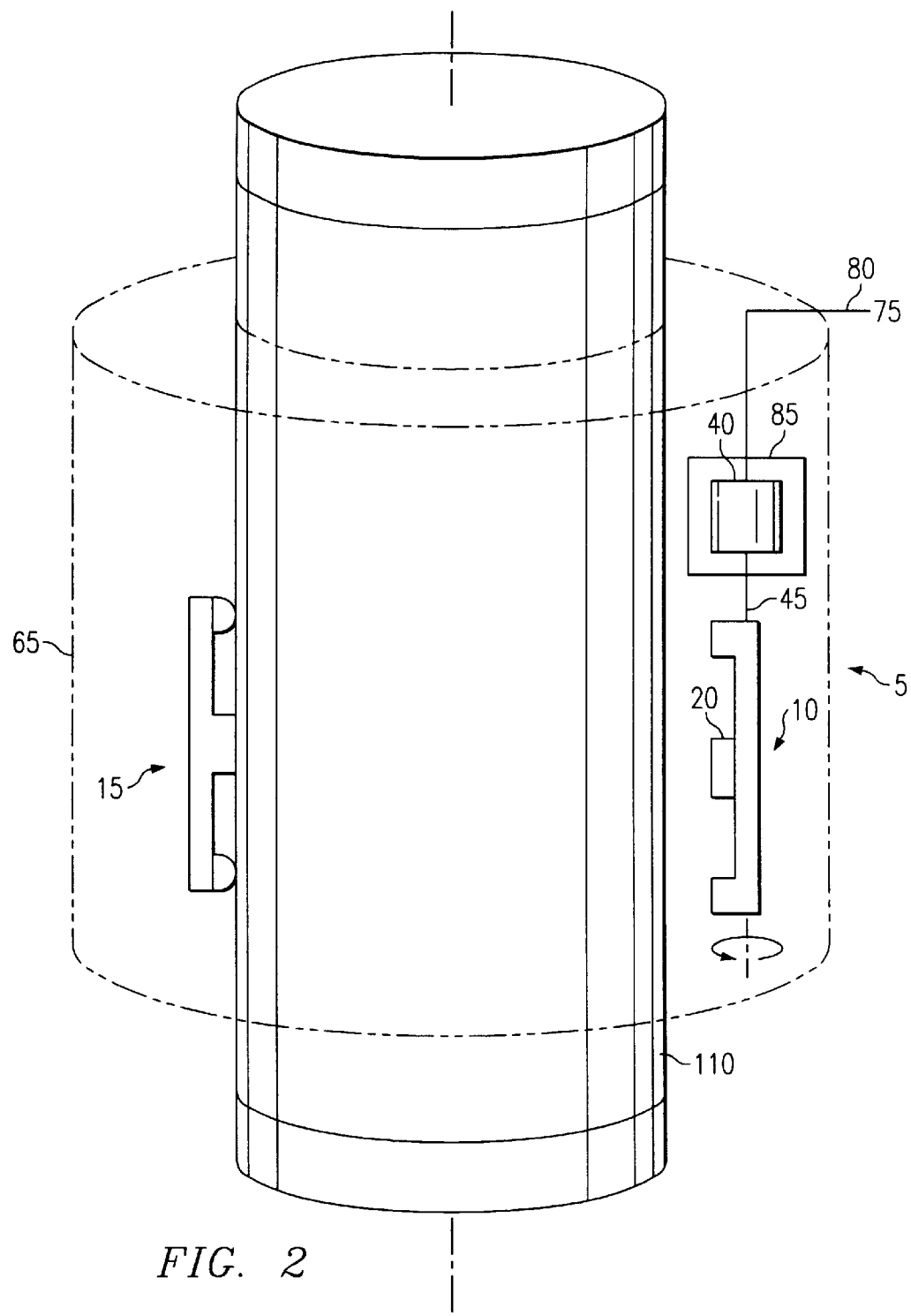
FIG. 2 illustrates a view of the invention showing a housing, sensor, magnet, and motor.

FIG. 2 is a further view of the embodiment shown on FIG. 1. FIG. 2 illustrates a housing 65 that secures the source piece 10, sensor piece 15, and motor 40 to a nonmagnetic cylindrical spool 110. The sensor piece 15 is attached to the housing 65 by bolts, screws, or other suitable fasteners. The source piece 10 is attached to the housing 65 by the shaft 45 and motor 40. The housing 65 wraps around the outside surface of the nonmagnetic cylindrical spool 110 and is firmly secured to the outside surface of the nonmagnetic cylindrical spool 110 by Velcro, hooks and receivers, or other suitable fasteners. The source piece 10 and sensor piece 15 are oriented within the housing 65 so that when the housing 65 is secured to the nonmagnetic cylindrical spool 110, the source piece 10 and sensor piece 15 are secured on opposite sides of the nonmagnetic cylindrical spool 110. When the housing 65 secures the sensor piece 15 to the nonmagnetic cylindrical spool 110, the three horizontal sections of the sensor piece 15 are pressed to the nonmagnetic cylindrical spool 110. The source piece 10 is secured to the nonmagnetic cylindrical spool 110 but is not in physical contact with the nonmagnetic cylindrical spool 110. The source piece 10 is horizontally rotatable about the vertical axis of the shaft 45 by the motor 40, and so should be disposed close to, but not touching the nonmagnetic cylindrical spool 110. The source piece 10 is connected to the motor 40 by the shaft 45 and oriented within the housing 65 so that a small space exists between the source piece 10 and the nonmagnetic cylindrical spool 110. The motor 40 is located within the housing 65. The motor 40 is preferably enclosed within a motor housing 85, which motor housing 85 is attached to the housing 65. The motor housing 85 may be attached to the housing 65 by bolts, screws, or other suitable fasteners. Advantageously, the motor 40 may be a pneumatic motor. Examples of available pneumatic motors include the Cooper Tools 21M1340-40 motor. An air supply 75 provides air to power the motor 40 through an air supply line 80. An opening in the housing 65 allows the air supply line 80 access to the motor 40. As shown, the shaft 45 connects the motor 40 to the source piece 10. Alternatively, the motor 40 may be an electric motor. Examples of available electric motors include the McMaster-Carr 6331K31 motor.

It will be appreciated that the invention is not limited to one sensor piece 15 secured to an opposite side of the nonmagnetic cylindrical spool 110 from the source piece 10, as illustrated on FIGS. 2, 3, 5, 8, 9, 10, 11, and 12. In alternative embodiments (not illustrated), the invention may comprise more than one sensor piece 15, with each sensor piece 15 advantageously disposed on the opposite side of the nonmagnetic cylindrical spool 110 from the source piece 10. In these alternative embodiments, the invention may also comprise one or more of these sensor pieces 15 joined together.

Figure 3:
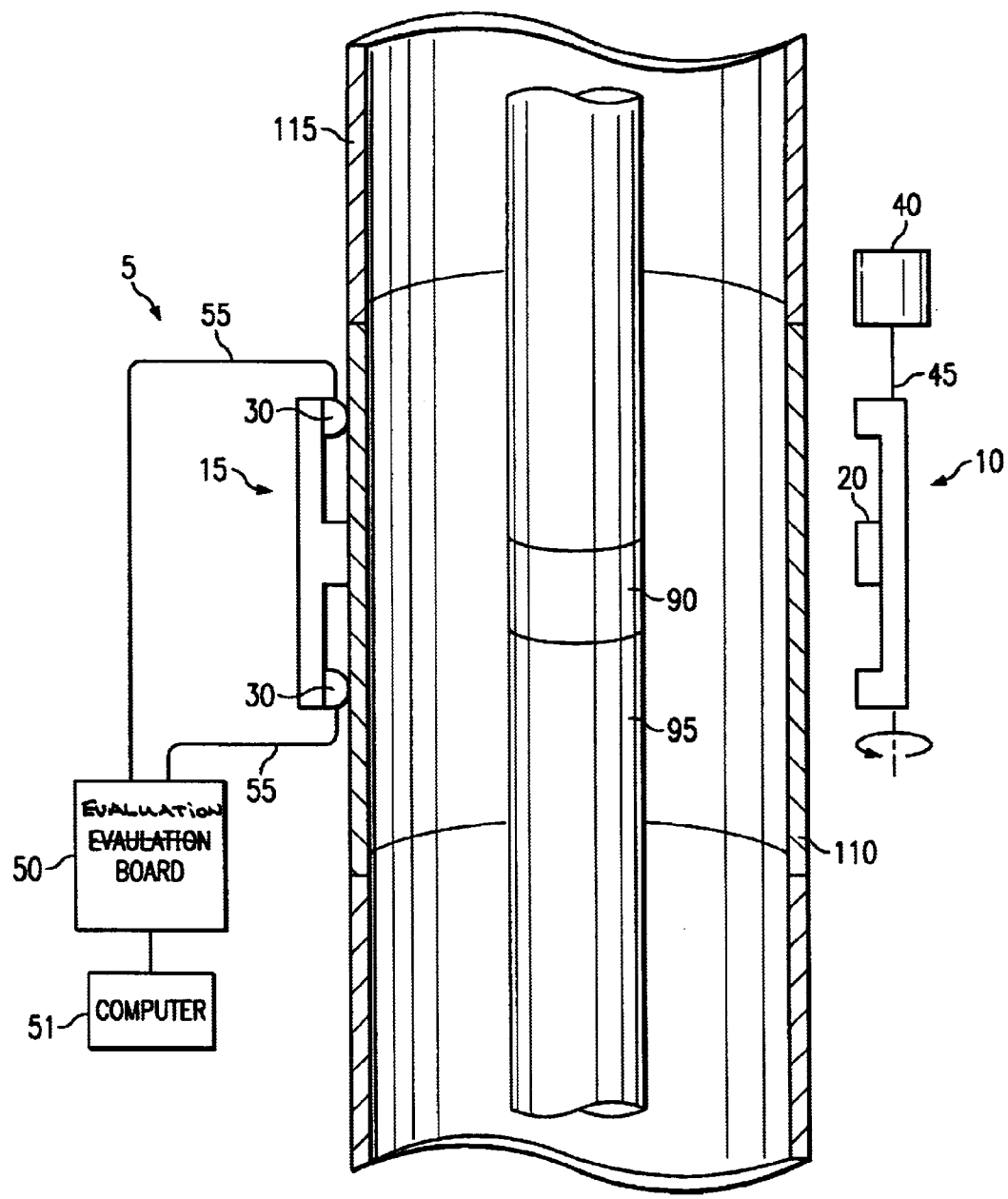
FIG. 3 illustrates a view of the invention showing the invention with a tubing string and a tool joint.

FIG. 3 is a further view of the embodiment depicted in FIG. 1 showing a nonmagnetic cylindrical spool 110 with a tubing string 95 and tool joint 90. As shown, the nonmagnetic cylindrical spool 110 is a section of a riser spool 115. The nonmagnetic cylindrical spool 110 comprises a nonmagnetic material, preferably nonmagnetic stainless steel. The source piece 10 is on the opposite side of the nonmagnetic cylindrical spool 110 from the sensor piece 15. The tubing string 95 and tool joint 90 are movable in or out of the nonmagnetic cylindrical spool 110.

It will be seen on FIG. 3 that the source piece 10 creates an alternating magnetic field across the nonmagnetic cylindrical spool 110 by the motor 40 rotating the source piece 10 horizontally 360 degrees about the vertical axis of the shaft 45. When the tubing string 95 is stripped through the nonmagnetic cylindrical spool 110, the sensors 30 detect the presence of the tubing string 95. When present, the tubing string 95 will cause a decrease in the magnetic field across the nonmagnetic cylindrical spool 110 created by the rotatable source piece 10. Upon detection of this decrease in the magnetic field, the sensors 30 notify the evaluation board 50 (via the evaluation board connectors 55) of such detected decrease. The evaluation board 50 advantageously converts this information into a digital form. A remotely located computer 51 may then receive and process the information from the evaluation board 50.

With further reference to FIG. 3, the presence of a tool joint 90 in the nonmagnetic cylindrical spool 110 will cause the sensors 30 to detect an even larger decrease in the magnetic field created by the rotating source piece 10. The evaluation board 50 receives and processes this information from the sensors 30 and then transmits this information on to the computer 51.

The computer 51 on FIG. 3 may optionally use threshold detection and waveform analysis techniques to differentiate between signals so as to detect the presence of tubing strings 95 or tool joints 90. By threshold detection, the computer 51 evaluates the readings transmitted by the sensors 30 and compares them to predetermined values expected for the presence of tubing strings 95 and tool joints 90 and to predetermined values when no tubing strings 95 or tool joints 90 are present. Such comparisons are selected to indicate to the computer 51 whether a tool joint 90 or tubing string 95 is present, or the initial presence of the tubing string 95 in the nonmagnetic cylindrical spool 110, or when the last of the tubing string 95 exits the nonmagnetic cylindrical spool 110.

Alternatively, the computer 51 may also evaluate the sensor 30 information by waveform analysis. In normal mode (i.e., magnet 20 rotating without tool joints 90 or tubing strings 95 present), the magnetic field creates a characteristic waveform that is known and identified by the computer 51. The change in the magnetic field, and thereby change in waveform, by the presence of a tubing string 95 is known and identified by the computer 51. In addition, the change in the magnetic field, and thereby further change in waveform, by the presence of the tool joint 90 is also known and identified by the computer 51. These waveform changes are recognized by the computer 51 again with reference to predetermined changes in waveforms expected during the presence of tubing strings 95, tool joints 90, or when the tubing string 95 initially enters the nonmagnetic cylindrical spool 110, or when the last of the tubing string 95 exits the nonmagnetic cylindrical spool 110.

Figure 4:
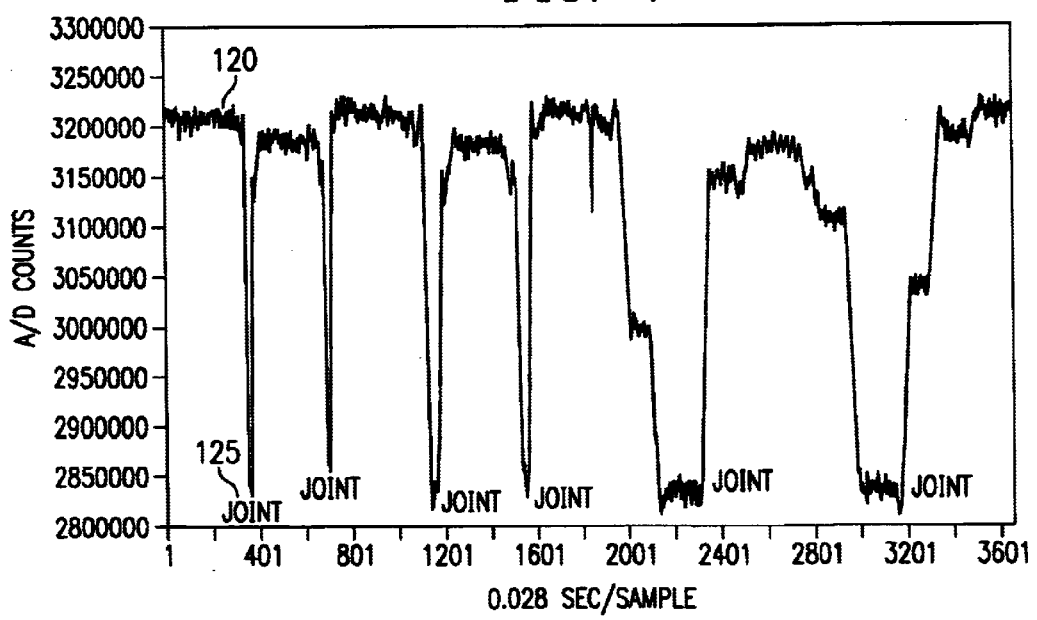
FIG. 4 depicts a waveform analysis showing presence of a tool joint.

FIG. 4 illustrates an exemplary waveform analysis of the alternating magnetic field by the computer 51 during expected normal operation of an embodiment such as is illustrated on FIG. 3. The y axis represents the sensor readings in counts. The x axis represents 0.028 seconds/sample reading. The readings in counts represent the presence of a jointed tubing string 95 with connecting tool joints 90 that are pulled through a sensor device 5, as shown on FIG. 3. As shown, the tubing string 95 is identified when entering the sensor device 5, registering a reading of over 3,200,000 counts. As the tubing string 95 is pulled through the sensor device 5, sensors 30 register these readings with the evaluation board 50 and then to the computer 51 on FIG. 3, which registers these readings on FIG. 4 as waveforms. It will be understood that the computer 51 on FIG. 3 will compare the registered waveform with predetermined changes in waveforms that are expected for the presence of tubing strings 95 and tool joints 90. With reference to the predetermined changes in waveforms, the computer 51 identifies these readings as a characteristic tubing string waveform 120, which is illustrated on FIG. 4. As a tool joint 90 is pulled through the sensor device 5, the sensors 30 register the decrease in counts from the magnetic reading, and the computer 51 registers these readings in waveform. Again from predetermined changes in waveforms, the computer 51 recognizes this waveform as a characteristic tool joint waveform 125, which is illustrated on FIG. 4.

Figure 5:
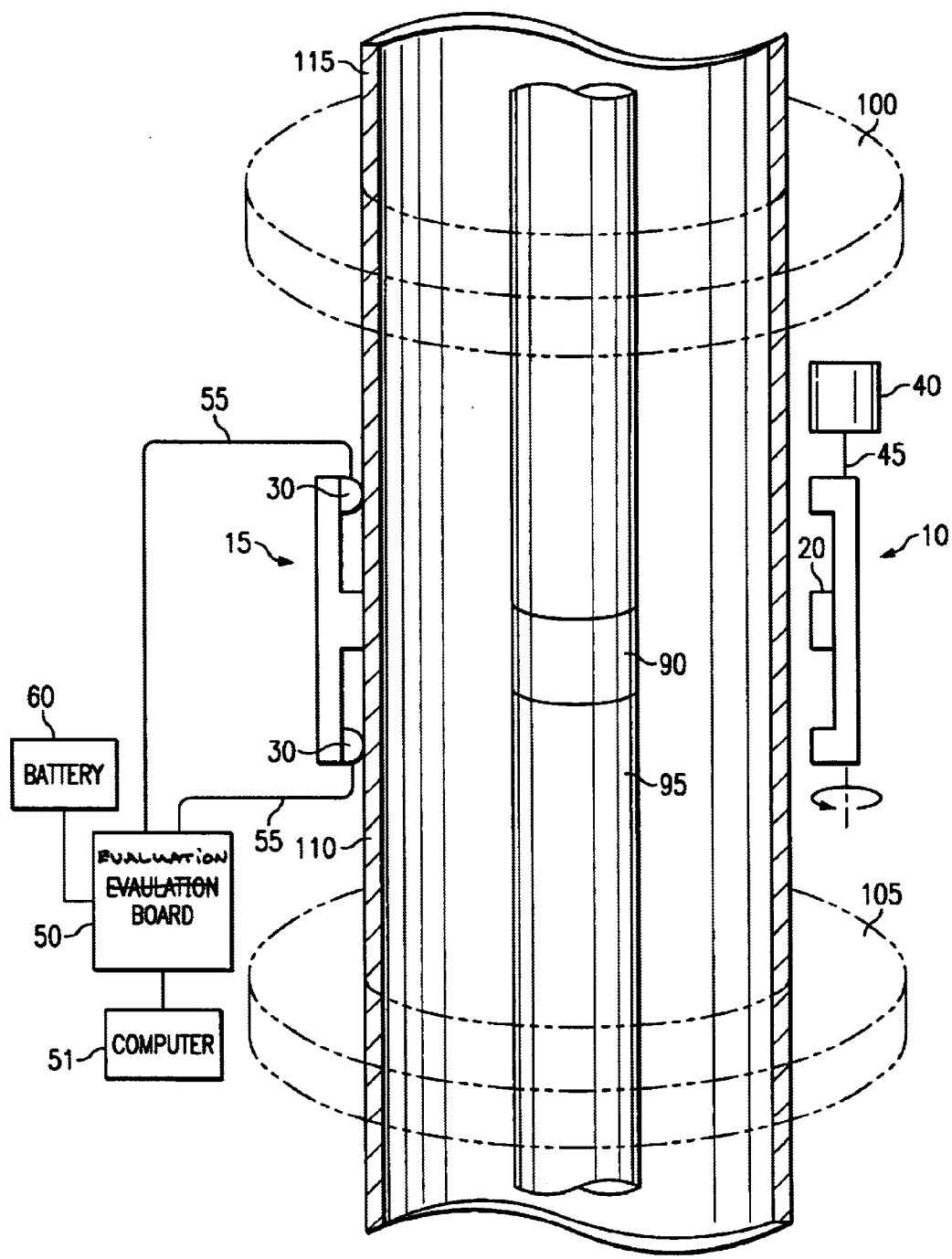
FIG. 5 illustrates a view of the invention showing blow out preventers.

FIG. 5 is a further view of the embodiment depicted in FIG. 1 showing a nonmagnetic cylindrical spool 110 and blow out preventers (BOPs) 100 and 105. As shown, an upper BOP 100 and a lower BOP 105 are connected to a riser spool 115. The nonmagnetic cylindrical spool 110 is a section of the riser spool 115. The nonmagnetic cylindrical spool 110 comprises a nonmagnetic material, preferably nonmagnetic stainless steel. The nonmagnetic cylindrical spool 110 separates the upper BOP 100 from the lower BOP 105. The source piece 10 is on the opposite side of the nonmagnetic cylindrical spool 110 from the sensor piece 15. The tubing string 95 and connecting tool joints 90 are moveable in or out of the riser spool 115.

It will be seen on FIG. 5 that the source piece 10 creates an alternating magnetic field across the nonmagnetic cylindrical spool 110 by the motor 40 rotating the source piece 10 horizontally 360 degrees about the vertical axis of the shaft 45. When the tubing string 95 is stripped through the nonmagnetic cylindrical spool 110, the sensors 30 detect the presence of the tubing string 95. When present, the tubing string 95 will tend to cause a decrease in the magnetic field across the nonmagnetic cylindrical spool 110 created by the rotating source piece 10. Upon detection of this decrease in the magnetic field, the sensors 30 notify the evaluation board 50 (via the evaluation board connectors 55) of such detected decrease. The evaluation board 50 processes this information and transmits it to the computer 51.

With further reference to FIG. 5, the evaluation board 50 and battery box 60 are located adjacent to the sensor piece 15. Alternatively, the evaluation board 50 and battery box 60 are remotely located, preferably on a structure supported by the Christmas tree. The computer 51 is shown located remotely from the sensor piece 15. In this embodiment, the computer 51 is also connected to an audio and/or visual alarm by a cable. The audio and/or visual alarm will preferably be located near an operator. This audio and/or visual alarm indicates to the operator the presence of the tool joint 90 in the nonmagnetic cylindrical spool 110. Upon this alarm, the operator may halt the movement of the tubing string 95 and open and close the appropriate BOPs. This audio and/or visual alarm may also notify the operator of the presence of the tubing string 95, or when the tubing string 95 initially enters the nonmagnetic cylindrical spool 110, or when the last of the tubing string 95 exits the nonmagnetic cylindrical spool 110.

The following describes an exemplary application of the present invention as embodied and illustrated on FIG. 5. In operation, as the tubing string 95 is stripped from the well bore, it can be seen on FIG. 5 that the tubing string 95 is pulled upwards through the riser spool 115. The lower BOP 105 is open, and the upper BOP 100 is closed. Both the upper BOP 100 and the lower BOP 105 are openable and closable around the tubing string 95, separating the high pressure of the well bore from the lower atmospheric pressure. The sections of the tubing string 95 are connected by tool joints 90. As the motor 40 rotates the permanent magnet 20, the permanent magnet 20 creates an alternating magnetic field across the nonmagnetic cylindrical spool 110. The sensors 30 measure the alternating magnetic field created by the permanent magnet 20 and transmit a signal to the evaluation board 50, which advantageously converts the signal into digital form. The evaluation board 50 then transmits this information to the computer 51, which continually monitors and processes these sensor 30 readings. When a tubing string 95 enters the nonmagnetic cylindrical spool 110 during stripping, the lower BOP 105 remains open, and the upper BOP 100 remains closed. The sensors 30 transmit a signal to the evaluation board 50 indicating presence of the tubing string 90 in the nonmagnetic cylindrical spool 110. The evaluation board 50 processes this signal and transmits this signal to the computer 51, which monitors and further processes the information. As a tool joint 90 enters the nonmagnetic cylindrical spool 110, the lower BOP 105 remains open, and the upper BOP 100 remains closed. The sensors 30 will identify the lower reading of the magnetic field caused by the tool joint 90. The sensors 30 will transmit the reading to the evaluation board 50. The evaluation board 50 will process this reading and transmit the reading to the computer 51, which will monitor and further process the reading. By analysis using techniques such as threshold detection or waveform analysis, the computer 51 will identify the presence of the tool joint 90 and notify the operator of the tool joint's 90 presence by audio and/or visual alarm.

Notified of the presence of the tool joint 90 in the nonmagnetic cylindrical spool 110 of FIG. 5, the operator will temporarily halt the stripping of the tubing string 95. With the upper BOP 100 remaining closed, the lower BOP 105 is then closed, and the nonmagnetic cylindrical spool 110 is depressurized to atmospheric pressure. After the nonmagnetic cylindrical spool 110 is depressurized, the lower BOP 105 remains closed, and the upper BOP 100 is opened. The stripping of the tubing string 95 is then resumed. When the tool joint 90 exits the upper BOP 100, the sensors 30 will transmit to the evaluation board 50 the increased magnetic readings. The evaluation board 50 will process this information and then transmit the information to the computer 51. The computer 51 will identify that no tool joint 90 is within the nonmagnetic cylindrical spool 110. The computer 51 will then notify the operator by audio and/or visual alarm that no tool joint 90 is present in the nonmagnetic cylindrical spool 110. The operator will then temporarily halt the movement of the tubing string 95. With the lower BOP 105 remaining closed, the upper BOP 100 will be closed, and the nonmagnetic cylindrical spool 110 will be re-pressurized to the pressure within the riser spool 115. After re-pressurization, the upper BOP 100 will remain closed, and the lower BOP 105 will be opened, followed by resumption of the stripping of the tubing string 95. When a tubing string 95 is moved into the well instead of stripped from the well, the same procedures apply in clearing the tool joints 90 of the BOPs but in converse order.

Figure 6:
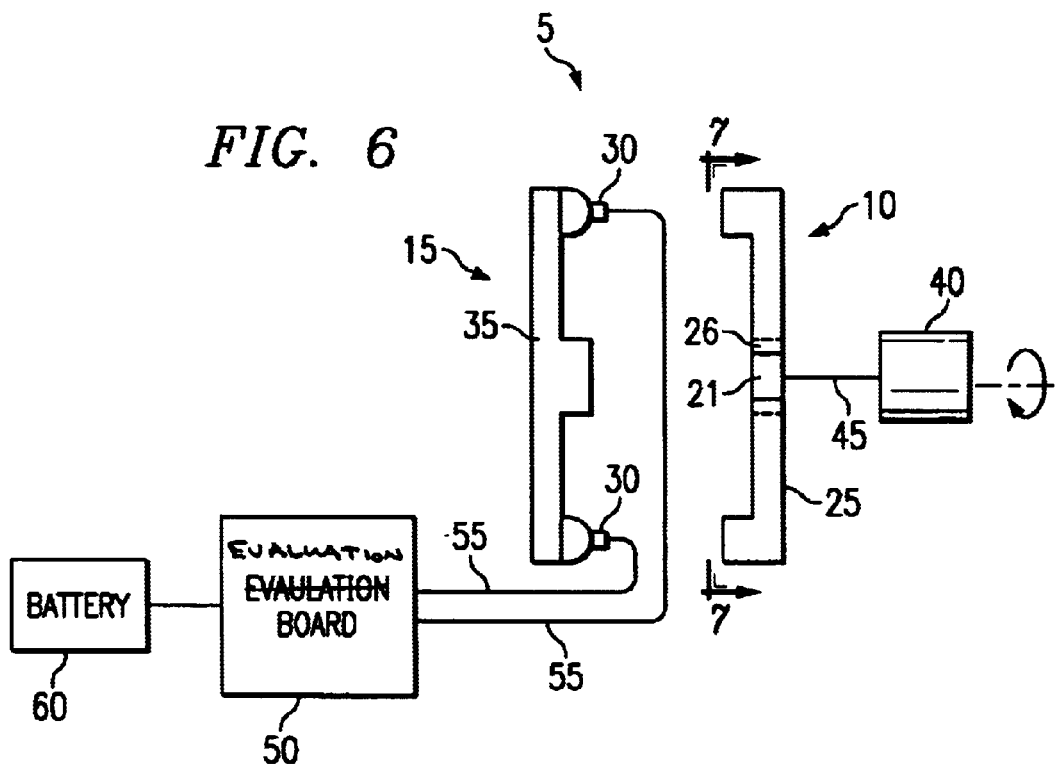
FIG. 6 illustrates an embodiment of the invention showing the motor connected to a magnet housing.

FIG. 6 is a further embodiment of the invention showing a sensor device 5 comprising a source piece 10, sensor piece 15 and with a motor 40 attached to a magnet housing 21. The source piece 10 includes a magnet housing 21 and a source field shaper 25. A permanent magnet (See FIG. 7) is enclosed within the magnet housing 21. The magnet housing 21 and source field shaper 25 comprise a non-corrosive, soft magnetically permeable material, such as iron. Because the permanent magnet exerts a magnetic field in all directions, the source field shaper 25 directs the magnetic field in the horizontal direction away from the source field shaper 25. As shown, the sensor piece 15 comprises sensors 30 and a sensor field shaper 35. The sensor field shaper 35 also comprises a non-corrosive, soft, magnetically permeable material, again such as iron. The source field shaper 25 includes a void section 26. The void section 26 comprises a removed section of the source field shaper 25. The magnet housing 21 is advantageously disposed within the void section 26. A motor 40 is attached to the magnet housing 21 by a shaft 45.

In the embodiment illustrated in FIG. 6, the source piece 10 comprises three sections, upper and lower horizontal sections and a vertical section. These three sections comprise the source field shaper 25. Alternatively, the source field shaper 25 may have more than two horizontal sections. The void section 26 and magnet housing 21 are located within the vertical section. The magnet housing 21 is rotatable 360 degrees by the motor 40 and shaft 45. The shaft 45 is secured to the magnet housing 21 by bolts, screws, or other suitable fasteners. The motor 40 rotates the magnet housing 21 about the horizontal axis of the shaft 45, thereby creating the alternating magnetic field. As further illustrated, an evaluation board 50 is connected to the sensors 30 by evaluation board connectors 55. A battery box 60 is connected to the evaluation board 50.

Figure 7:
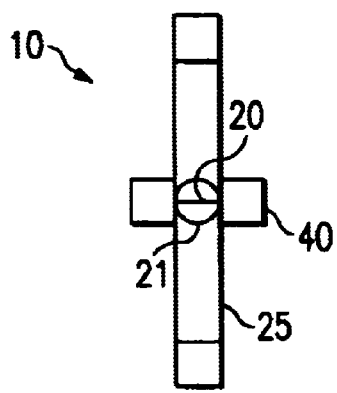
FIG. 7 is a cross sectional view as shown on FIG. 6.

FIG. 7 is a cross sectional frontal view as shown on FIG. 6. FIG. 7 illustrates the source piece 10 comprising a permanent magnet 20, magnet housing 21, and source field shaper 25. As shown, the permanent magnet 20 is disposed within the magnet housing 21. The motor 40 rotates the permanent magnet 20 and magnet housing 21.

Figure 8:
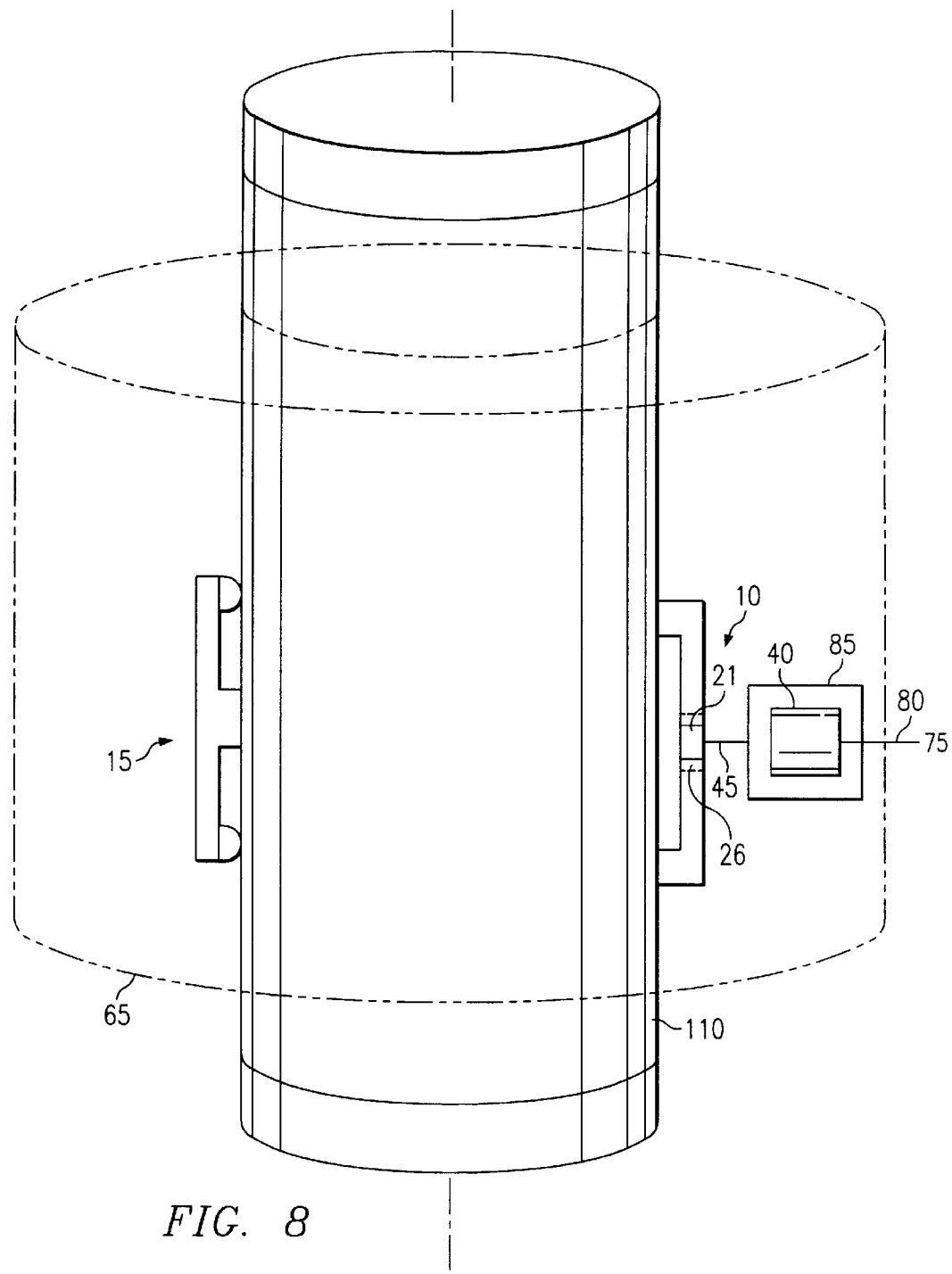
FIG. 8 illustrates a view of the invention showing a housing, sensor, and a motor connected to a magnet housing.

FIG. 8 illustrates a further view of the embodiment depicted on FIG. 6 showing a housing 65 that secures the source piece 10, sensor piece 15, and motor 40 to a nonmagnetic cylindrical spool 110. The sensor piece 15 is attached to the housing 65 by bolts, screws, or other suitable fasteners. The source piece 10 is attached to the housing 65 by bolts, screws, or other suitable fasteners. The housing 65 wraps around the outside surface of the nonmagnetic cylindrical spool 110 and is firmly secured to the outside surface of the nonmagnetic cylindrical spool 110 by Velcro, hooks and receivers, or other suitable fasteners. The source piece 10 and sensor piece 15 are oriented within the housing 65 so that when the housing 65 is secured to the nonmagnetic cylindrical spool 110, the source piece 10 and sensor piece 15 are secured on opposite sides of the nonmagnetic cylindrical spool 110. When the housing 65 secures the sensor piece 15 to the nonmagnetic cylindrical spool 110, the three horizontal sections of the sensor piece 15 are pressed to the nonmagnetic cylindrical spool 110. When the housing 65 secures the source piece 10 to the nonmagnetic cylindrical spool 110, the two horizontal sections of the source piece 10 are also pressed to the nonmagnetic cylindrical spool 110. The magnet housing 21 is disposed within the void section 26 and is rotatable about an axis that is orthogonal to the cylindrical axis of the nonmagnetic cylindrical spool 110. FIG. 8 illustrates that such orthogonal rotation is about shaft 45 of motor 40. The source piece 10 is connected to the motor 40 by the attachment of the shaft 45 to the magnet housing 21. The motor 40 is located within the housing 65. The motor 40 is enclosed within a motor housing 85, which motor housing 85 is attached to the housing 65. The motor housing 85 may be attached to the housing 65 by bolts, screws, or other suitable fasteners. Advantageously, the motor 40 may be a pneumatic motor. An air supply 75 provides air to power the motor 40 through an air supply line 80. An opening in the housing 65 allows the air supply line 80 access to the motor 40. As shown, the shaft 45 connects the motor 40 to the source piece 10. Alternatively, the motor 40 may be an electric motor.

Figure 9:
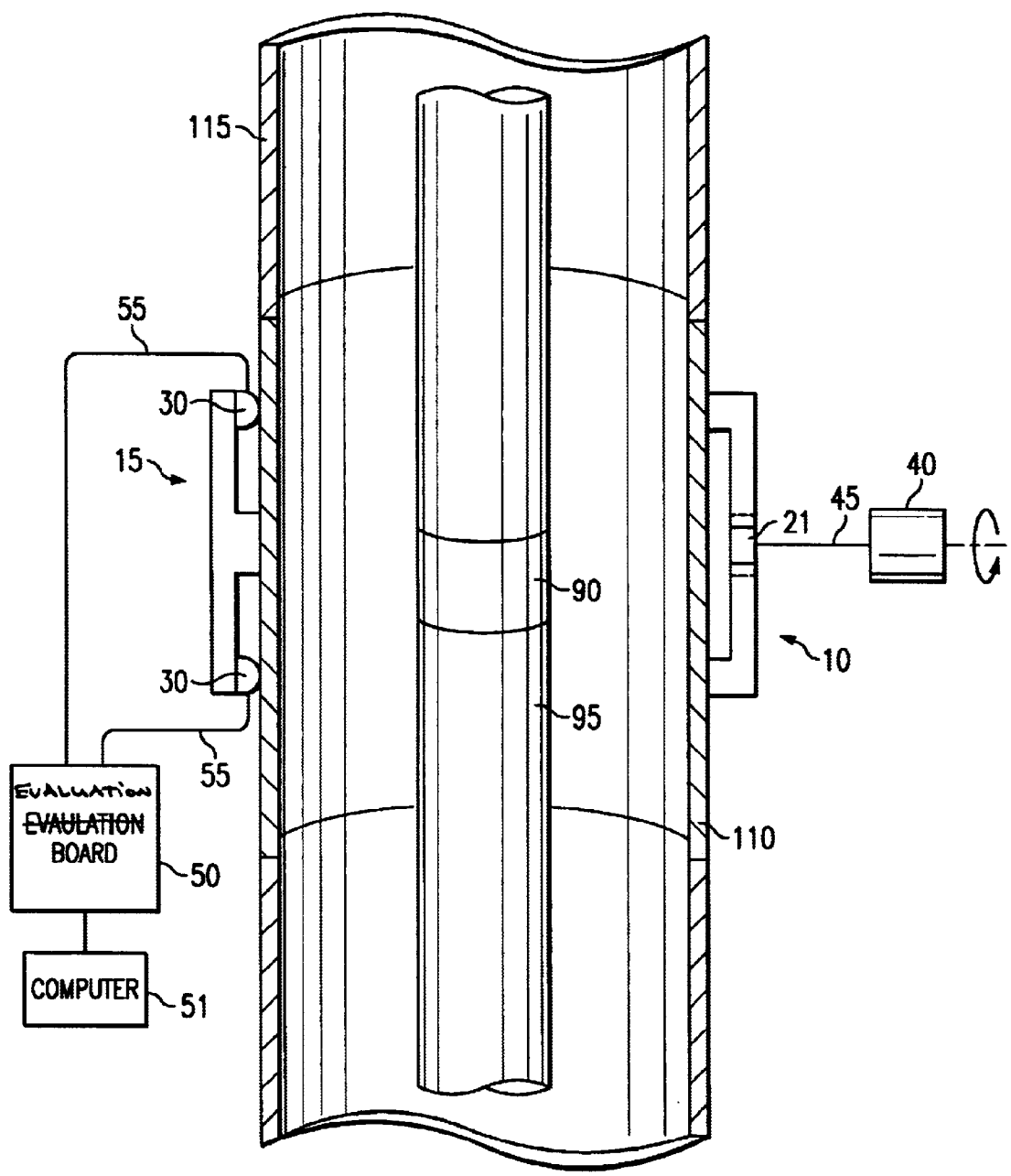
FIG. 9 illustrates a view of the invention showing the invention with a tubing string, tool joint, and a motor connected to a magnet housing.

FIG. 9 is a further view of the embodiment illustrated in FIG. 6 showing a nonmagnetic cylindrical spool 110 with a tubing string 95 and tool joint 90. The nonmagnetic cylindrical spool 110 comprises a nonmagnetic material, preferably nonmagnetic stainless steel. As shown, the nonmagnetic cylindrical spool 110 will be understood to be a section of a riser spool 115. The source piece 10 is on the opposite side of the nonmagnetic cylindrical spool 110 from the sensor piece 15. The tubing string 95 and tool joint 90 are movable in or out of the nonmagnetic cylindrical spool 110.

It will be seen on FIG. 9 that the source piece 10 creates an alternating magnetic field across the nonmagnetic cylindrical spool 110 by the motor 40 rotating the magnet housing 21, which encloses the permanent magnet 20. The rotation of the magnet housing 21 is 360 degrees about shaft 45, and the axis of rotation is disposed orthogonal to the cylindrical axis of the nonmagnetic cylindrical spool 110. When the tubing string 95 is stripped through the nonmagnetic cylindrical spool 110, the sensors 30 detect the presence of the tubing string 95. When present, the tubing string 95 will cause a decrease in the magnetic field across the nonmagnetic cylindrical spool 110 created by the rotatable permanent magnet 20. Upon detection of this decrease in the magnetic field, the sensors 30 notify the evaluation board 50 (via the evaluation board connectors 55) of such detected decrease. The evaluation board 50 advantageously converts this information into digital form. A remotely located computer 51 then receives and processes this information from the evaluation board 50.

With further reference to FIG. 9, the presence of a tool joint 90 in the nonmagnetic cylindrical spool 110 will cause the sensors 30 to detect an even larger decrease in the magnetic field created by the rotating permanent magnet 20. The evaluation board 50 receives and processes this information from the sensors 30 and then transmits this information on to the computer 51 for further processing.

Figure 10:
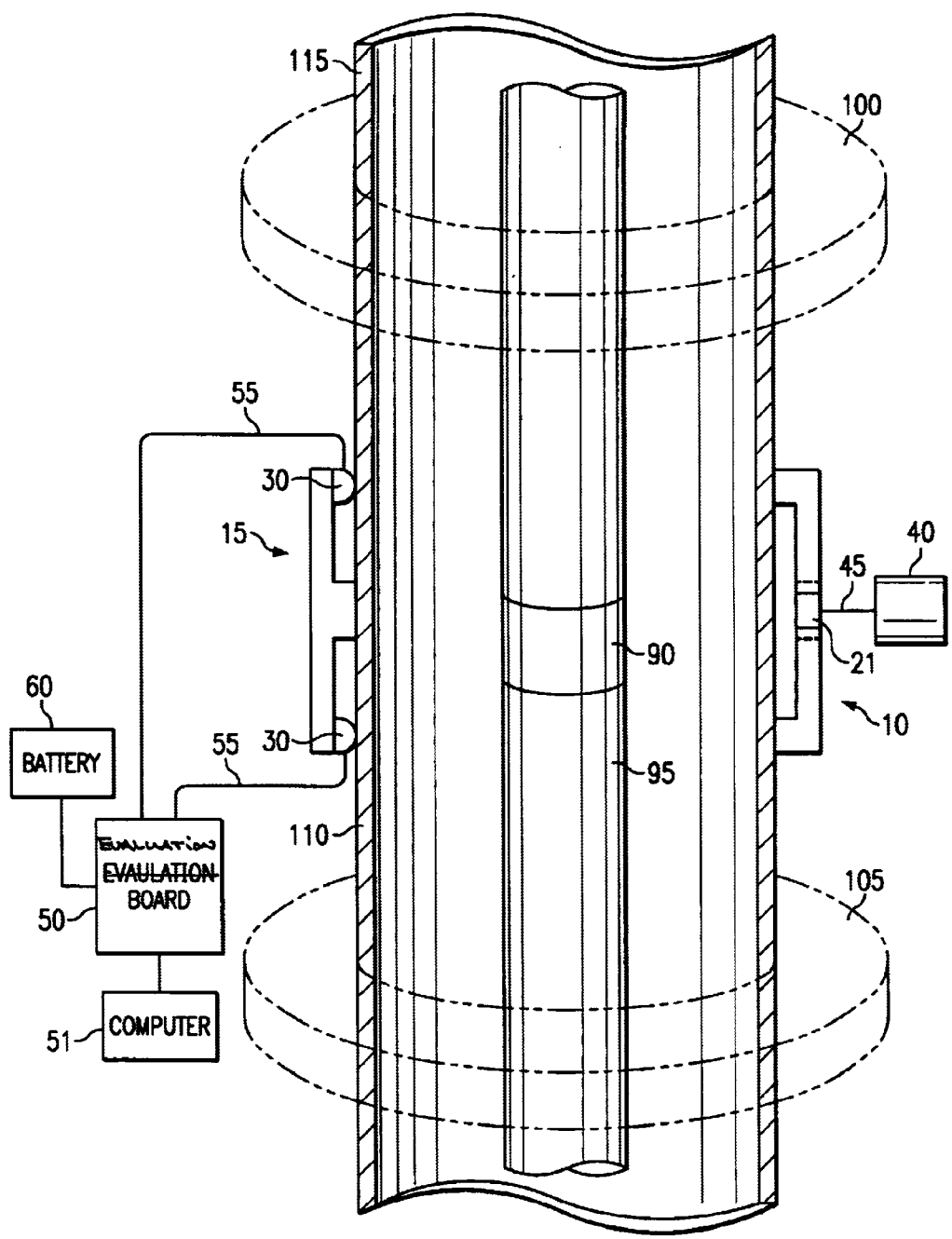
FIG. 10 illustrates a view of the invention showing blow out preventers and a motor connected to a magnet housing.

FIG. 10 is a further view of the embodiment depicted in FIG. 6 showing a nonmagnetic cylindrical spool 110 and blow out preventers (BOPs) 100 and 105. As shown, an upper BOP 100 and a lower BOP 105 are connected to a riser spool 115. The nonmagnetic cylindrical spool 110 is a section of the riser spool 115. The nonmagnetic cylindrical spool 110 comprises a nonmagnetic material, preferably nonmagnetic stainless steel. The nonmagnetic cylindrical spool 110 separates the upper BOP 100 from the lower BOP 105. The source piece 10 is on the opposite side of the nonmagnetic cylindrical spool 110 from the sensor piece 15. The tubing string 95 and connecting tool joints 90 are moveable in or out of the riser spool 115.

It will be seen on FIG. 10 that the source piece 10 creates an alternating magnetic field across the nonmagnetic cylindrical spool 110 by the motor 40 rotating the magnet housing 21, which encloses the permanent magnet 20. The rotation of magnet housing 21 is 360 degrees about shaft 45. When the tubing string 95 is stripped through the nonmagnetic cylindrical spool 110, the sensors 30 detect the presence of the tubing string 95. When present, the tubing string 95 will tend to cause a decrease in the magnetic field across the nonmagnetic cylindrical spool 110 created by the rotatable magnet 20. Upon detection of this decrease in the magnetic field, the sensors 30 notify the evaluation board 50 (via the evaluation board connectors 55) of such detected decrease. The evaluation board 50 processes this information and transmits it to the computer 51 for further processing.

With further reference to FIG. 10, the evaluation board 50 and battery box 60 are shown located adjacent to the sensor piece 15. Alternatively, the evaluation board 50 and battery box 60 may be located remotely, preferably on a structure supported by the Christmas tree. The computer 51 is remotely located from the sensor piece 15. In this embodiment, the computer 51 is also connected to an audio and/or visual alarm by a cable. The audio and/or visual alarm will preferably be located near an operator. This audio and/or visual alarm indicates to the operator the presence of the tool joint 90 in the nonmagnetic cylindrical spool 110. Upon this alarm, the operator may halt the movement of the tubing string 95 and open and close the appropriate BOPs. This audio and/or visual alarm may also notify the operator of the presence of the tubing string 95, or when the tubing string 95 initially enters the nonmagnetic cylindrical spool 110, or when the last of the tubing string 95 exits the nonmagnetic cylindrical spool 110.

In operation, FIG. 10 is analogous to the application depicted in FIG. 5 except that the motor 40 rotates the magnet housing 21 and thereby rotates the enclosed permanent magnet 20.

Figure 11:
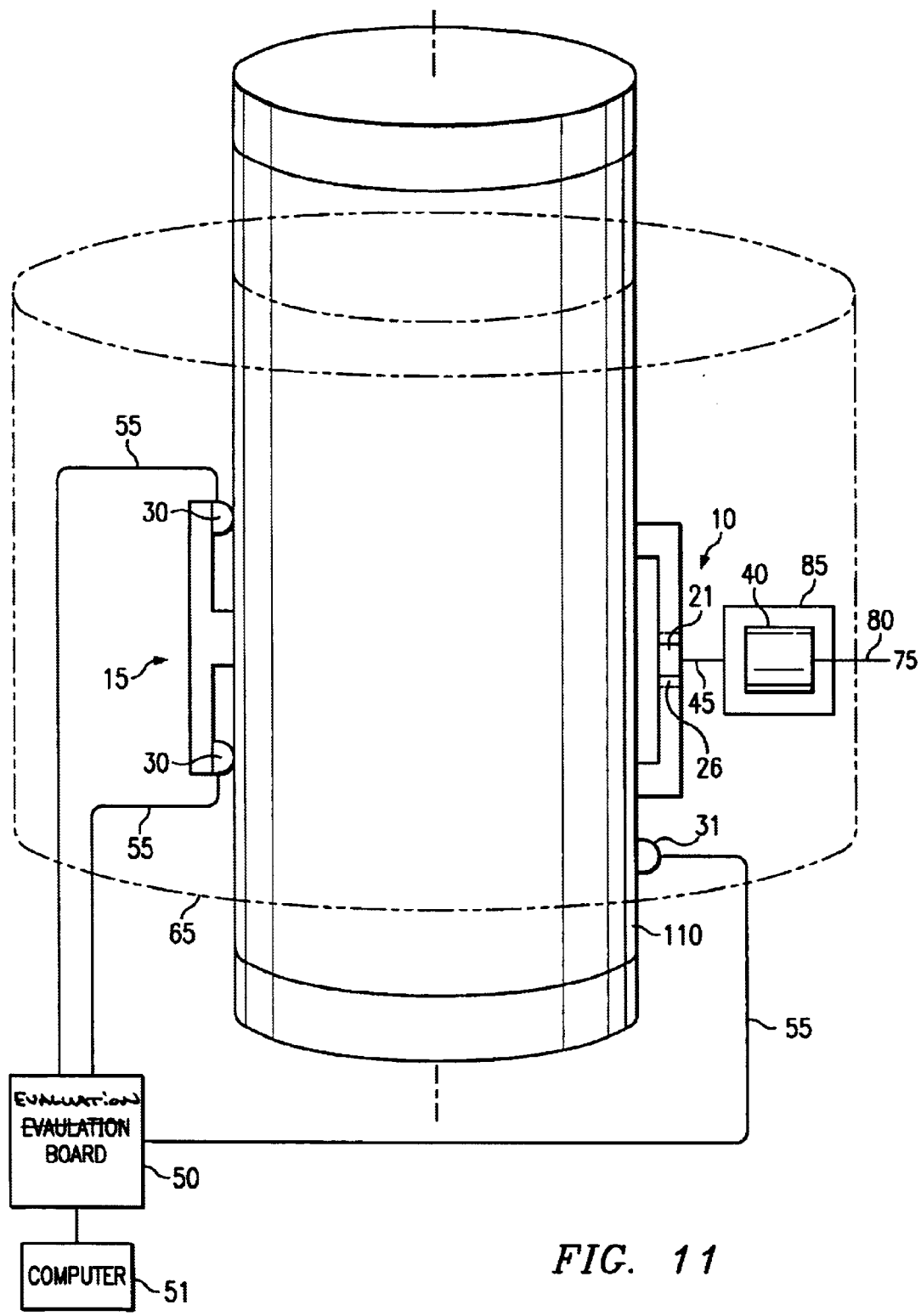
FIG. 11 illustrates an embodiment of the invention showing a synchronization sensor disposed substantially diametrically across the nonmagnetic cylindrical spool from the sensor piece.

FIG. 11 illustrates an alternative embodiment of the invention depicting a synchronization sensor 31 disposed to monitor the rotation of the permanent magnet 20, which is enclosed within the magnet housing 21. The synchronization sensor 31 is pressed to the nonmagnetic cylindrical spool 110 and secured by the housing 65. The synchronization sensor 31 is attached to the housing 65 by bolts, screws, or other suitable fasteners. A variety of sensor technologies known in the art may be used for the synchronization sensor 31 but preferably conventional Hall effect sensors are used. In the alternative, Anisotropic Magnetoresistive sensors or Giant Magnetoresistive sensors could be used for sensor technology instead of Hall effect devices.

It will be seen on FIG. 11 that the source piece 10, sensor piece 15, and synchronization sensor 31 are oriented within the housing 65 so that when the housing 65 is secured to the nonmagnetic cylindrical spool 110, the source piece 10 and synchronization sensor 31 are disposed on the opposite side of the nonmagnetic cylindrical spool 110 from the sensor piece 15. The synchronization sensor 31 is disposed in close proximity to the source piece 10. The synchronization sensor 31 and sensor piece 15 are connected to the evaluation board 50 by evaluation board connectors 55. When the motor 40 rotates the magnet housing 21 and thereby rotates the permanent magnet 20, an alternating magnetic field is created across the nonmagnetic cylindrical spool 110, which alternating magnetic field results in alternating maximum magnetic flux values and minimum magnetic flux values being detectable and measurable across the nonmagnetic cylindrical spool 110.

It will be seen on FIG. 11 that the synchronization sensor 31 measures the magnetic field created by the source piece 10. The synchronization sensor 31 does not measure the magnetic field across the nonmagnetic cylindrical spool 110, which is measured by the sensor piece 15. Instead, the synchronization sensor 31 continuously monitors the magnetic field created by the source piece 10 and transmits measured flux values to the evaluation board 50 via the evaluation board connectors 55. The evaluation board 50 will receive this signal and transmit it to the computer 51, which computer 51 will process and evaluate this information to determine whether a maximum or minimum magnetic flux value is at that instant being exerted. Upon an evaluation that the source piece 10 is creating a maximum magnetic flux value, the computer 51 transmits a signal via the evaluation board 50 to the sensors 30. Upon receipt of this signal identifying the maximum magnetic flux value, the sensors 30 will take their reading of the magnetic field across the nonmagnetic cylindrical spool 110. Unless the sensors 30 receive the signal from the computer 51 identifying a maximum magnetic flux value, the sensors 30 will not take their reading. A technical advantage of synchronizing the sensor 30 readings to the maximum magnetic flux value is that the effects of electrical and magnetic noise interferences are averaged out and minimized.

In an alternative embodiment that is not illustrated, the synchronization sensor 31 may be attached to the source field shaper 25. In this alternative embodiment, the synchronization sensor 31 may be connected to the source field shaper 25 by bolts, screws, or other suitable fasteners.

Figure 12:
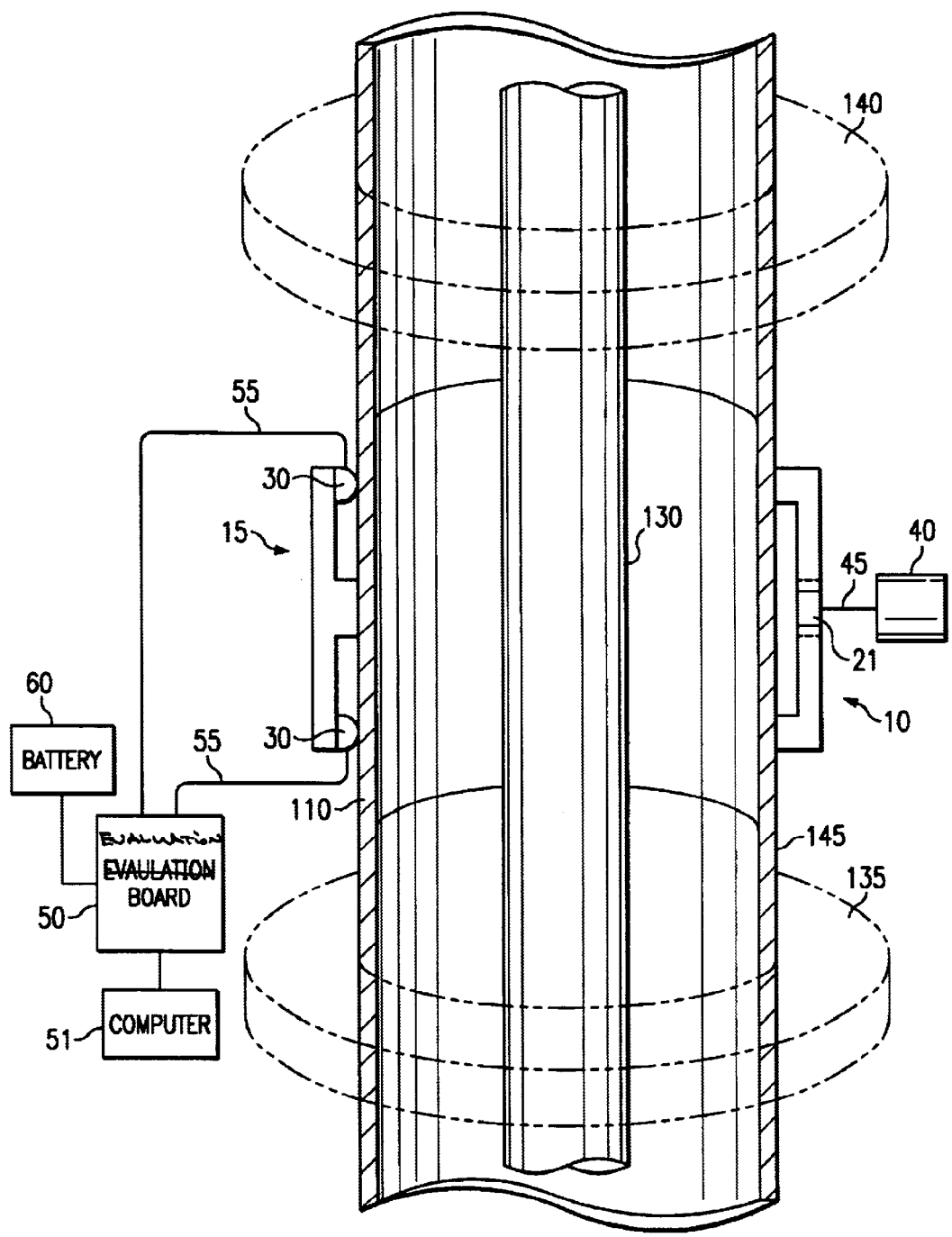
FIG. 12 illustrates an embodiment of the invention showing the invention with a coiled tubing string.
Figure 1:
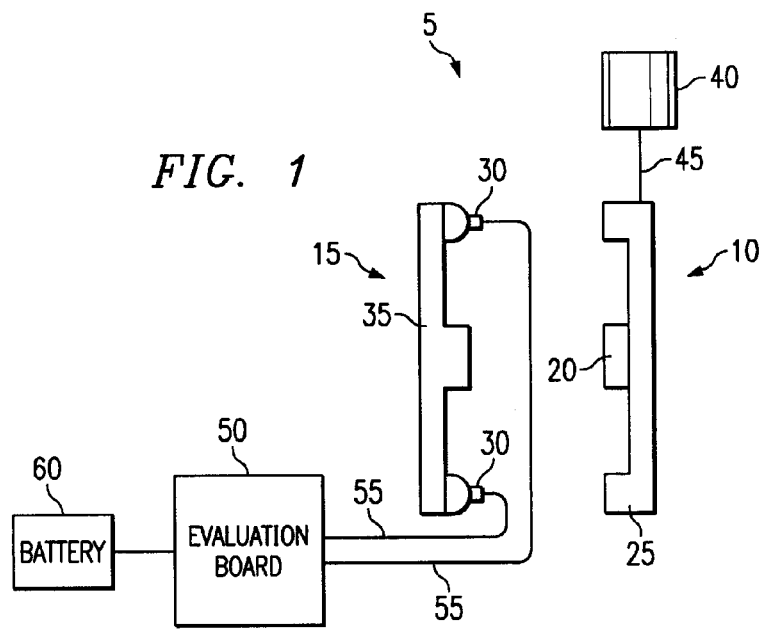
Figure 4:
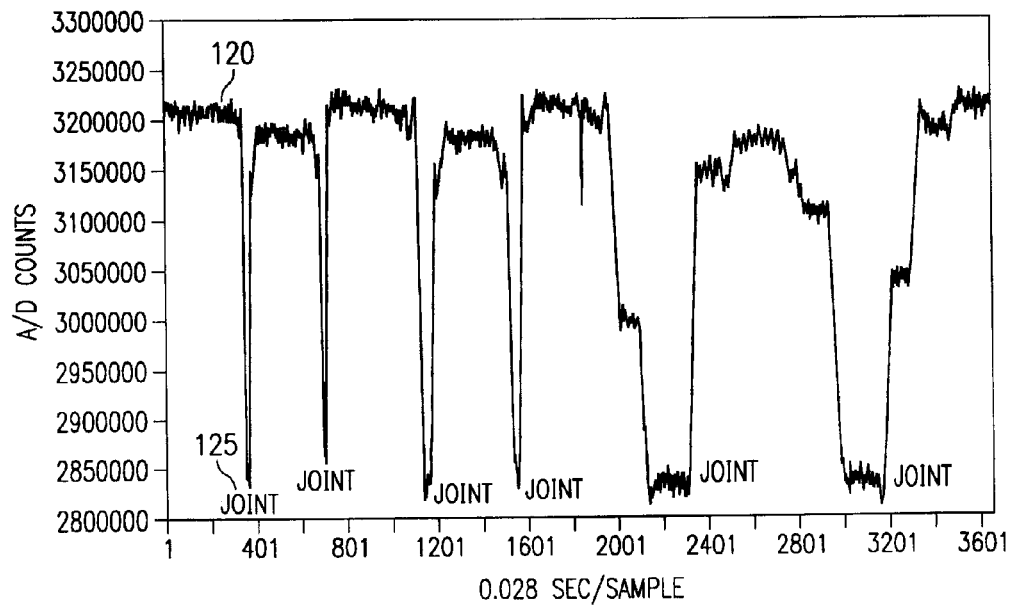
Figure 3:
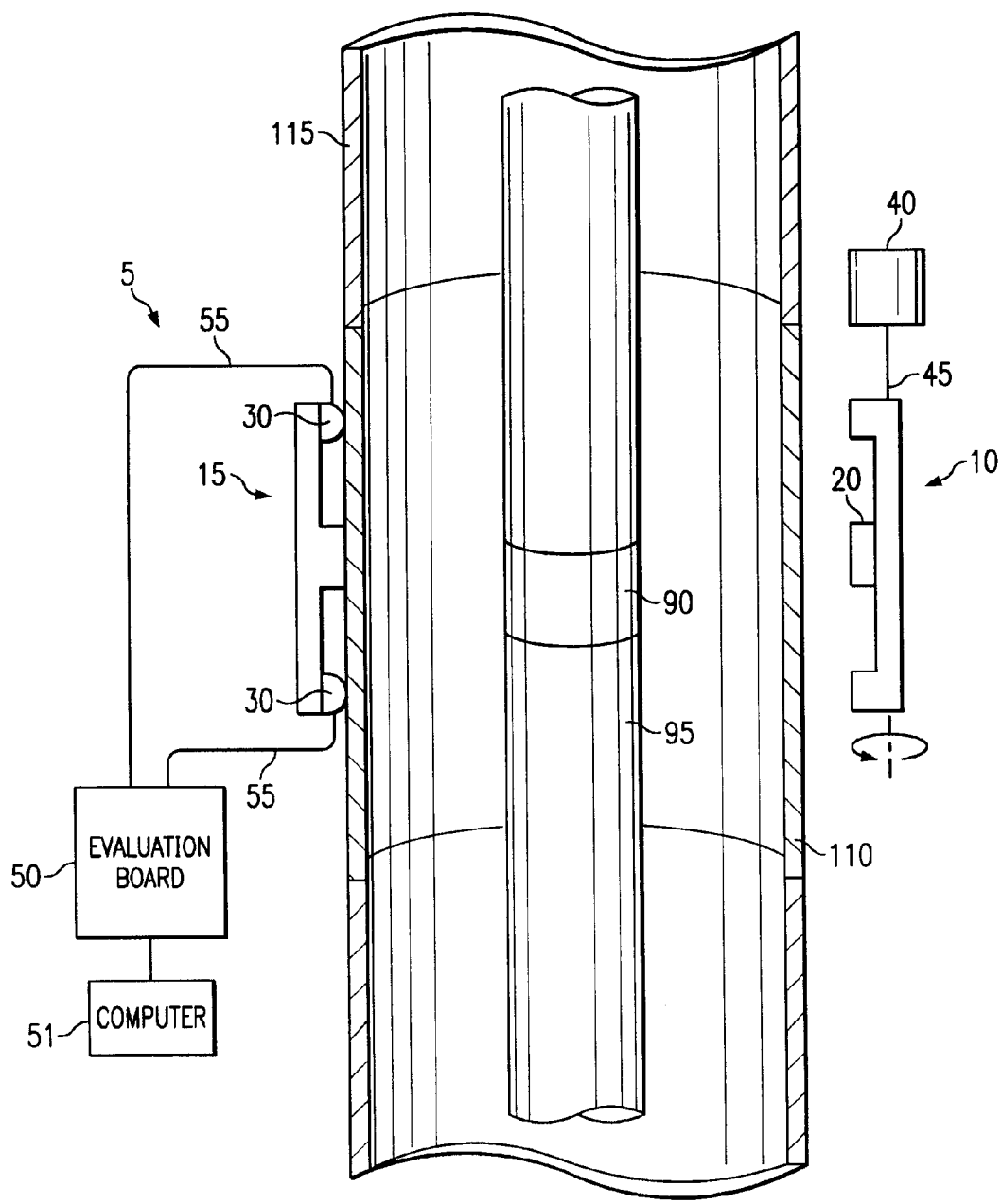
Figure 5:
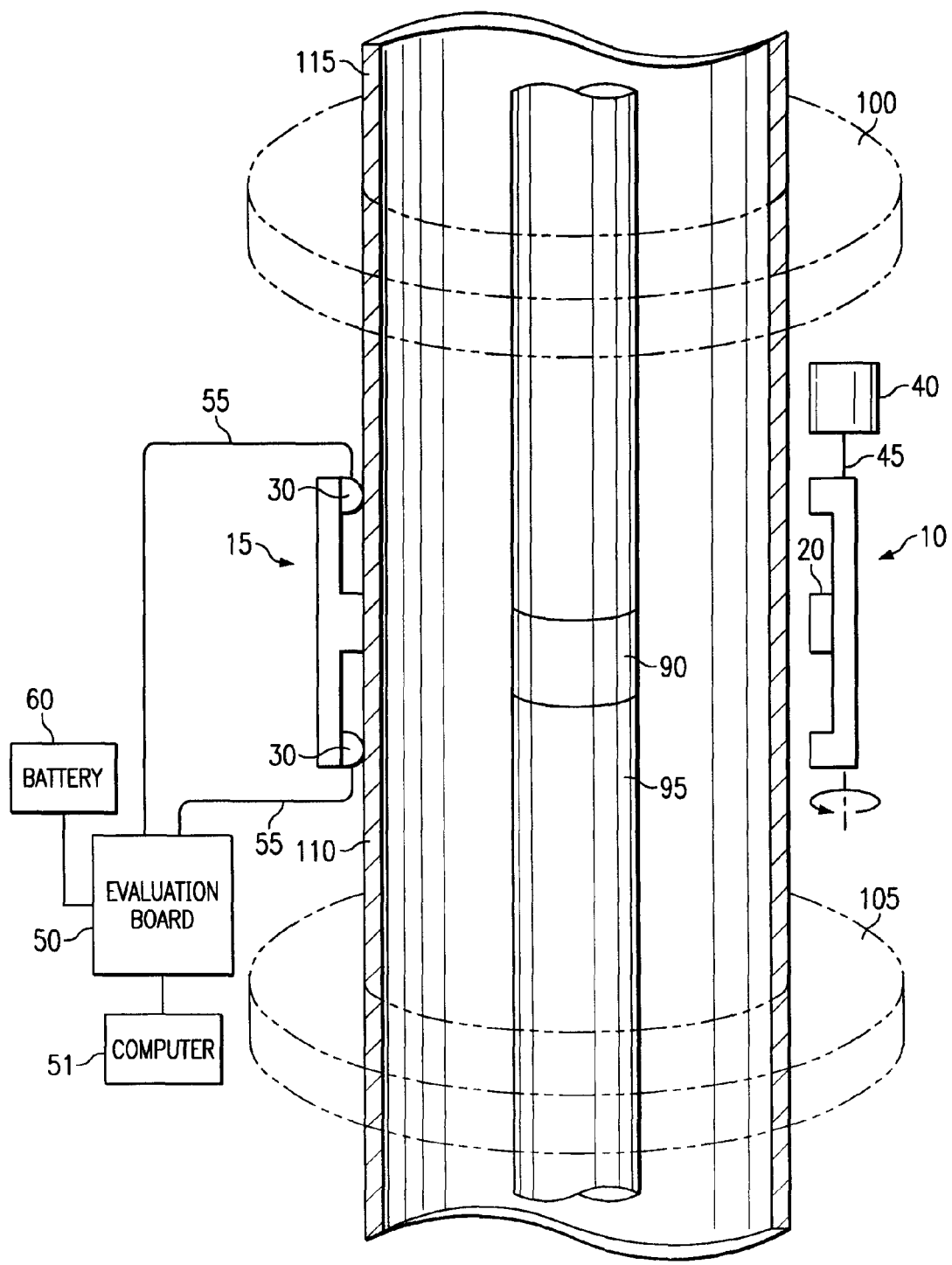
Figure 6:
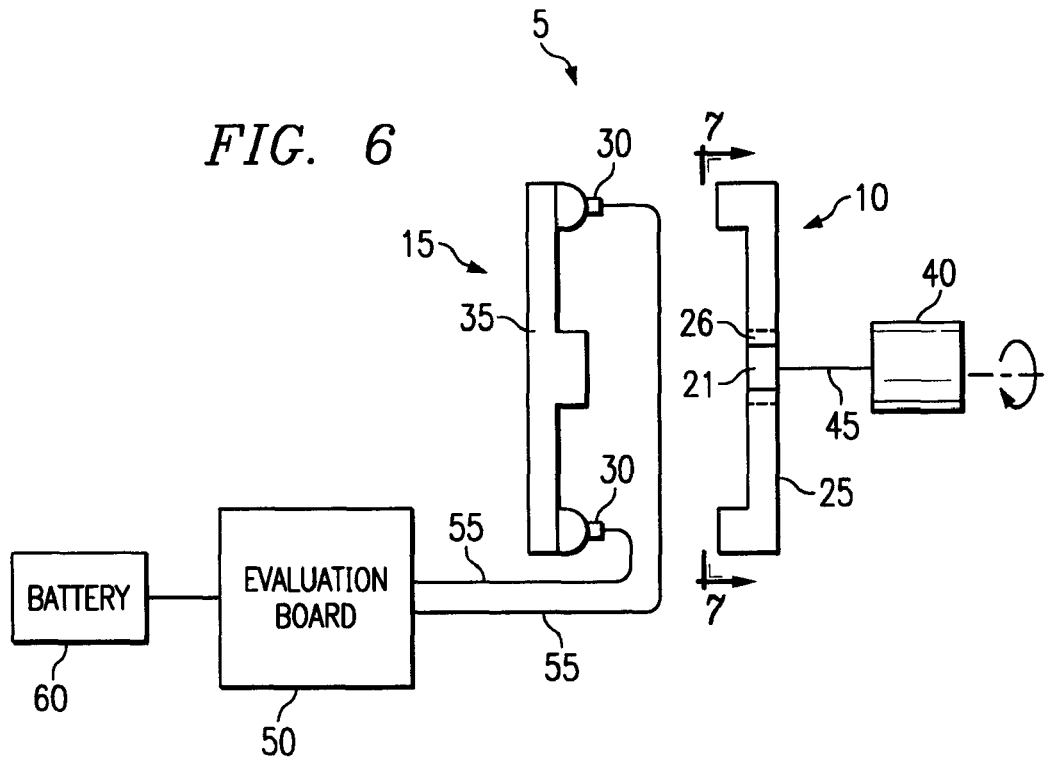
Figure 7:
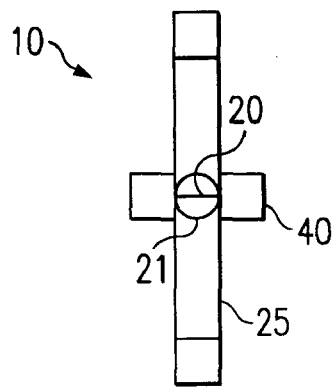
Figure 9:
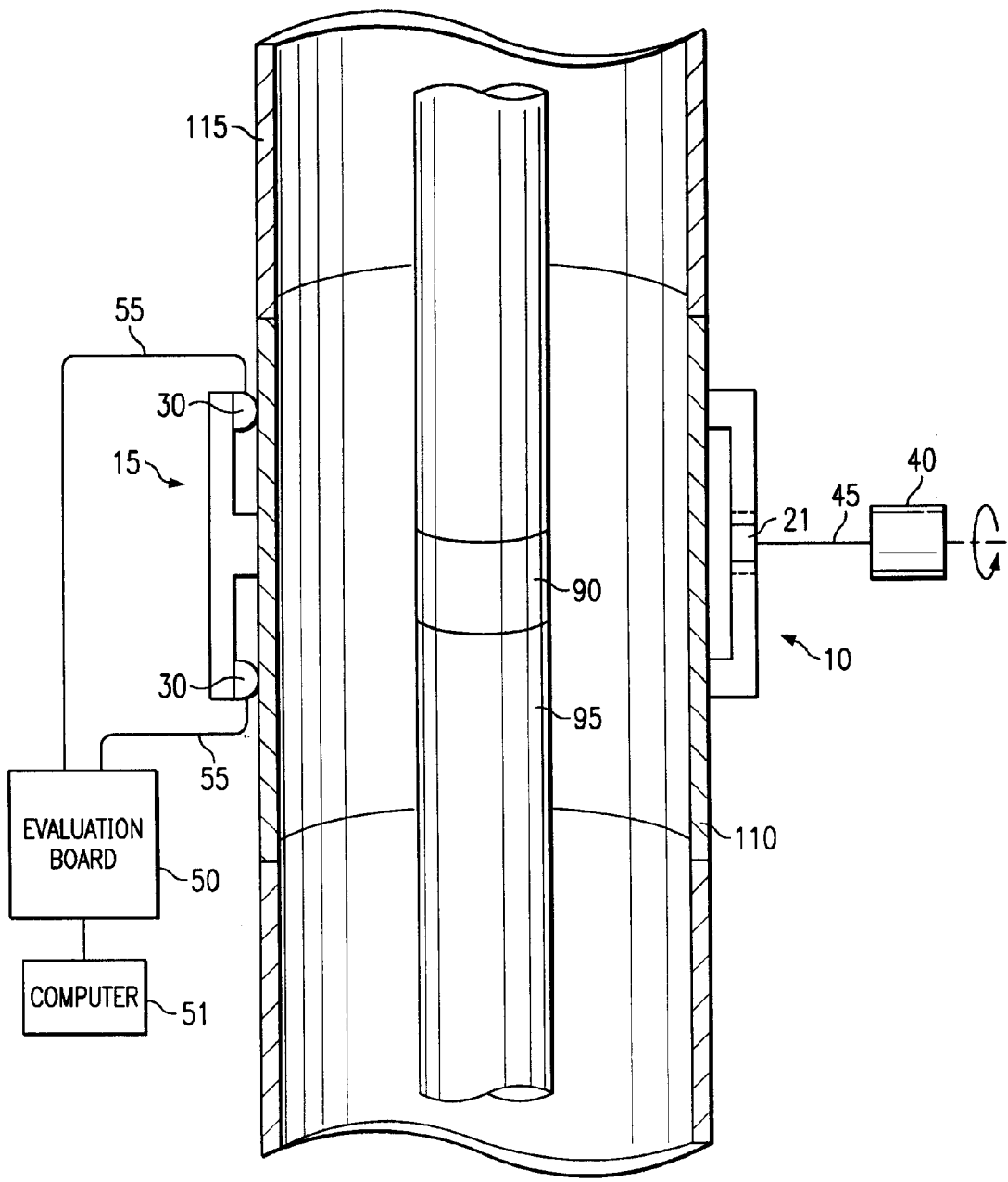
Figure 10:
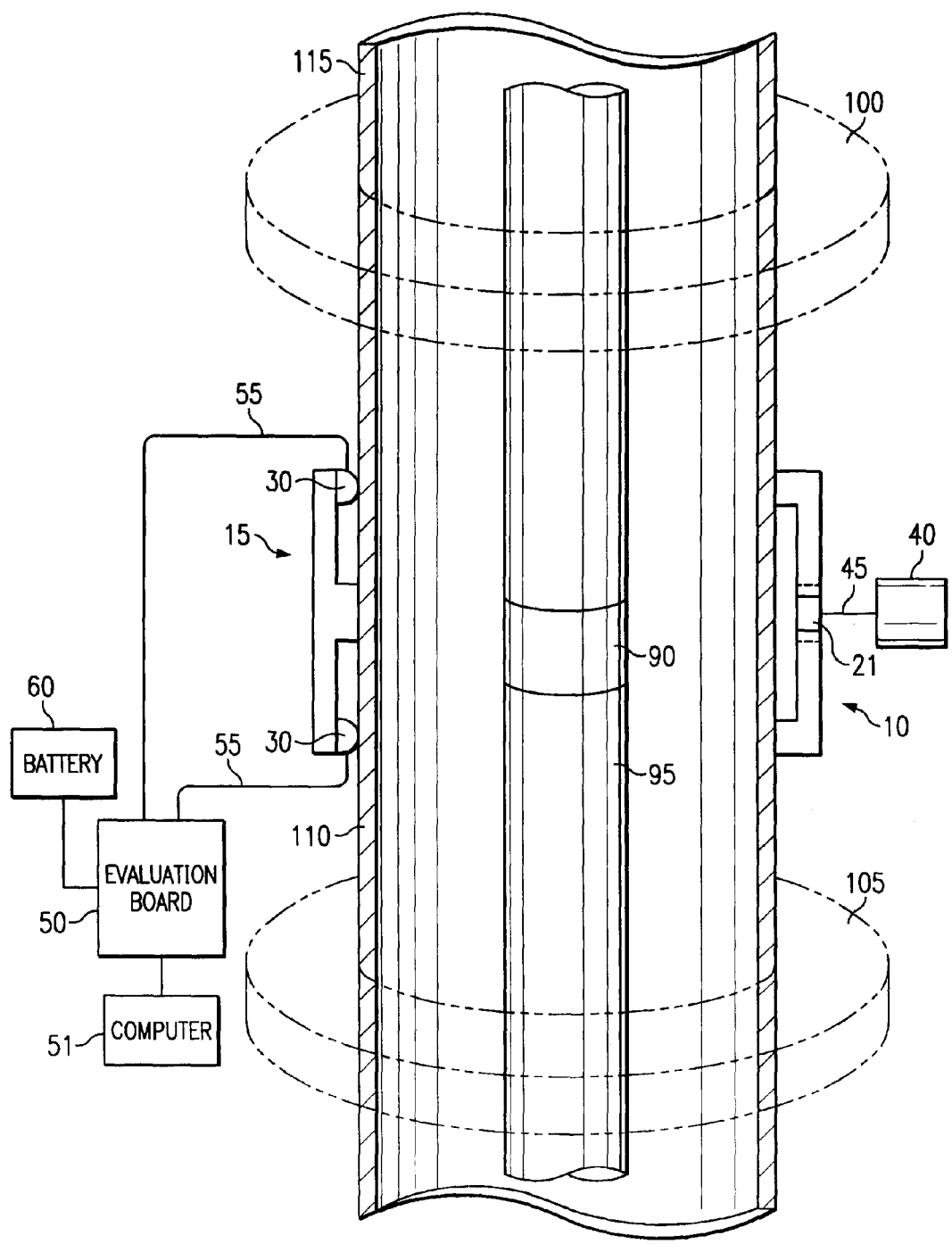
Figure 11:
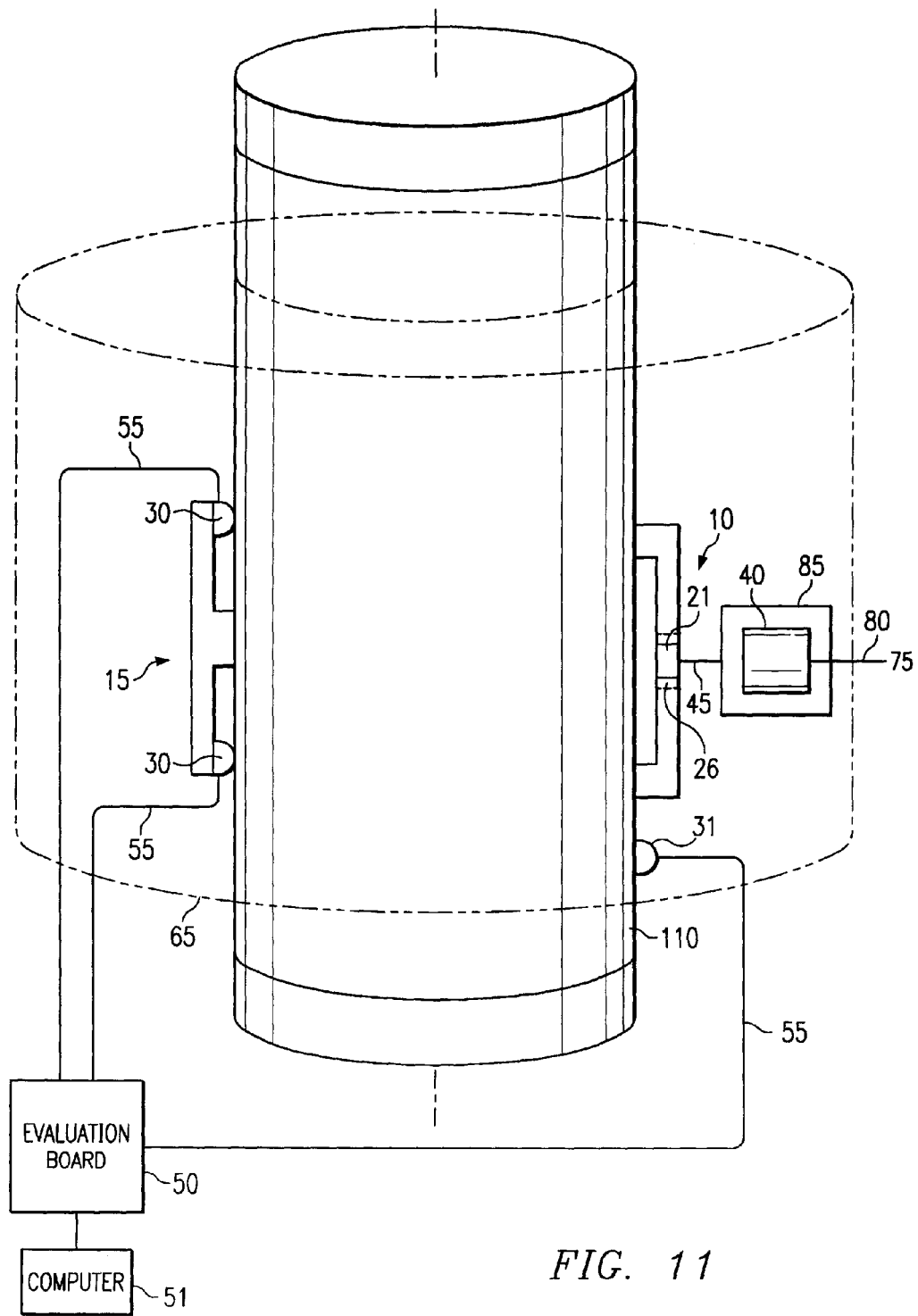
Figure 12:
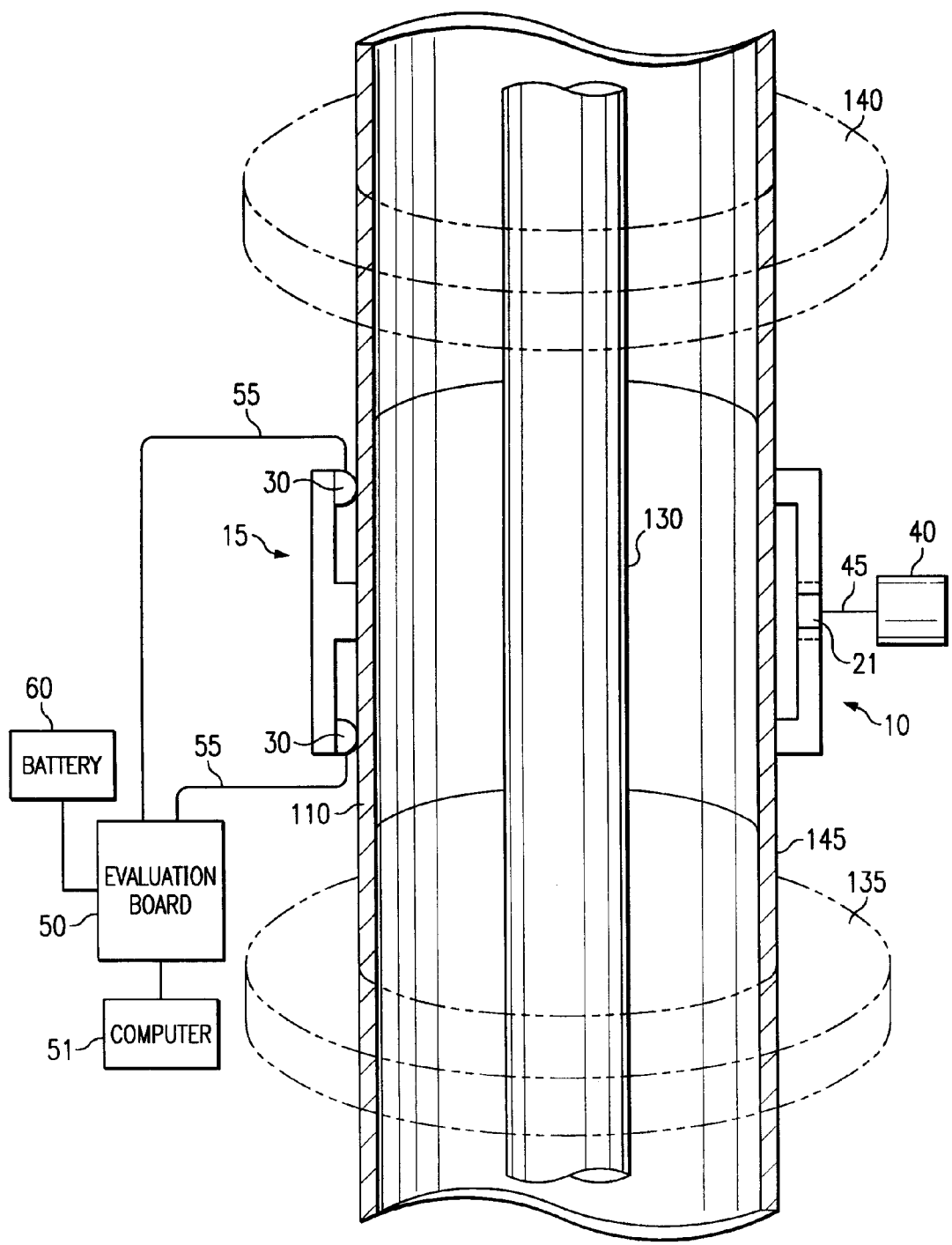

FIG. 12 illustrates a further embodiment of the invention showing a coiled tubing string 130, a crown valve 135, and a BOP stack 140. The crown valve 135 is the top valve in the Christmas tree of a well. As shown, an adapter spool 145 connects the nonmagnetic cylindrical spool 110 to the crown valve 135. The nonmagnetic cylindrical spool 110 separates the BOP stack 140 from the adapter spool 145 and crown valve 135. The BOP stack 140 may have a plurality of BOPs comprising at least one stripping BOP. The different types of BOPs comprising the BOP stack are well known in the art. Examples of available BOPs include stripping, blind, and cutter BOPs. The source piece 10 is on the opposite side of the nonmagnetic cylindrical spool 110 from the sensor piece 15. The coiled tubing string 130 is moveable in or out of the crown valve 135 and the BOP stack 140.

It will be seen on FIG. 12 that the source piece 10 creates an alternating magnetic field across the nonmagnetic cylindrical spool 110 by the motor 40 rotating the magnet housing 21, which encloses the permanent magnet 20. The rotation of magnet housing 21 is 360 degrees about shaft 45. When the coiled tubing string 130 is stripped through the nonmagnetic cylindrical spool 110, the sensors 30 detect the presence of the coiled tubing string 130. When the last of the coiled tubing string 130 exits the nonmagnetic cylindrical spool 110, the exit of the coiled tubing string 130 will tend to cause an increase in the magnetic field across the nonmagnetic cylindrical spool 110 created by the rotatable magnet 20. Upon detection of this increase in the magnetic field, the sensors 30 notify the evaluation board 50 (via the evaluation board connectors 55) of such detected increase. The evaluation board 50 processes this information and transmits it to the computer 51 for further processing.

With further reference to FIG. 12, the evaluation board 50 and battery box 60 are shown located adjacent to the sensor piece 15. Alternatively, the evaluation board 50 and battery box 60 may be located remotely, preferably on a structure supported by the Christmas tree. The computer 51 is remotely located from the sensor piece 15. In this embodiment, the computer 51 is also connected to an audio and/or visual alarm by a cable. The audio and/or visual alarm will preferably be located near an operator. This audio and/or visual alarm indicates to the operator the exit of the last of the coiled tubing string from the nonmagnetic cylindrical spool 110. Upon this alarm, the operator may halt the movement of the coiled tubing string 130 and close the crown valve 135. This audio and/or visual alarm may also notify the operator when the coiled tubing string 130 initially enters the nonmagnetic cylindrical spool 110. The invention is not limited to the nonmagnetic cylindrical spool 110 separating the adapter spool 145 and crown valve 135 from the BOP stack 140. Alternatively, a spacer spool (not illustrated) may separate the BOP stack 140 from the nonmagnetic cylindrical spool 110.

The following describes an exemplary application of the present invention as embodied and illustrated on FIG. 12. In operation, as the coiled tubing string 130 is stripped from the well bore, it can be seen on FIG. 12 that the coiled tubing string 130 is pulled upwards through the crown valve 135, nonmagnetic cylindrical spool 110, and the BOP stack 140. The crown valve 135 is open and the stripping BOPs of the BOP stack 140 are closed. Both the crown valve 135 and the stripping BOPs of the BOP stack 140 are openable and closable, with the stripping BOPs of the BOP stack 140 openable and closable around the coiled tubing string 130, separating the high pressure of the well bore from the lower atmospheric pressure. As the motor 40 rotates the permanent magnet 20, the permanent magnet 20 creates an alternating magnetic field across the nonmagnetic cylindrical spool 110. The sensors 30 measure the alternating magnetic field created by the permanent magnet 20 and transmit a signal to the evaluation board 50, which advantageously converts the signal into digital form. The evaluation board 50 then transmits this information to the computer 51, which continually monitors and processes these sensor 30 readings. When the coiled tubing string 130 is passing through the nonmagnetic cylindrical spool 110 during stripping, the crown valve 135 remains open and the stripping BOPs of the BOP stack 140 remain closed. The sensors 30 transmit a signal to the evaluation board 50 indicating the presence of the coiled tubing string 130 in the nonmagnetic cylindrical spool 110. The evaluation board 50 processes this signal and transmits this signal to the computer 51, which monitors and further processes the information. As the last of the coiled tubing string 130 exits the nonmagnetic cylindrical spool 110, the crown valve 135 may be closed and the stripping BOPs of the BOP stack 140 remain closed. The sensors 30 will identify the higher reading of the magnetic field caused by the exit of the coiled tubing string 130. The sensors 30 will transmit the reading to the evaluation board 50. The evaluation board 50 will process this reading and transmit the reading to the computer 51, which will monitor and further process the reading. By analysis using techniques such as threshold detection or waveform analysis (as functionally described earlier), the computer 51 will identify the exit of the coiled tubing string 130 and notify the operator of the coiled tubing string's 130 exit by audio and/or visual alarm.

Notified of the exit of the coiled tubing string 130 from the nonmagnetic cylindrical spool 110 of FIG. 12, the operator will temporarily halt the stripping of the coiled tubing string 130. With the stripping BOPs of the BOP stack 140 remaining closed, the crown valve 135 is then closed, and the adapter spool 145 and nonmagnetic cylindrical spool 110 are depressurized to atmospheric pressure. After the nonmagnetic cylindrical spool 110 and adapter spool 145 are depressurized, the crown valve 135 remains closed, and the stripping BOPs of the BOP stack 140 remain closed. The stripping of the coiled tubing string 130 is then resumed. When the coiled tubing string 130 exits the BOP stack 140, the stripping BOPs of the BOP stack 140 may be opened. When a coiled tubing string 130 is moved into the well instead of stripped from the well, the same procedures apply in maintaining the well pressure but in converse order.

It will be understood that the invention is not limited to a magnet housing 21 that encloses a permanent magnet 20. In alternative embodiments that are not illustrated, the permanent magnet 20 is not enclosed within a magnet housing 21. The permanent magnet 20 may be secured directly to the shaft 45 instead. The permanent magnet 20 may be secured to the shaft 45 by bolts, screws, or other suitable fasteners.

It will be further understood that the invention is not limited to an evaluation board 50 and computer 51 that receive and evaluate magnetic readings from the sensors 30. One alternative embodiment (not illustrated), may comprise an analog to digital conversion board and a control panel. A suitable example of a control panel includes but is not limited to the MEDC Ltd. GP2 control panel. The analog to digital converter is remotely located from the sensors 30, and preferably the analog to digital converter may be secured within the housing 65. The control panel is remotely located from the sensors 30, preferably on a structure supported by the Christmas tree. The analog to digital converter will process readings from the sensors 30 and/or the synchronization sensor 31 and then transmit these processed signals on to the control panel. The control panel may optionally use threshold detection and waveform analysis (as functionally described earlier) to differentiate between readings during the insertion or stripping of tubing strings 95 so as to detect the presence of tool joints 90, tubing strings 95, or the initial presence of the tubing string 95 in the nonmagnetic cylindrical spool 110, or to detect when the last of the tubing string 95 exits the nonmagnetic cylindrical spool 110 and during the insertion or stripping of coiled tubing strings 130 so as to detect when the last of the coiled tubing string 130 exits the nonmagnetic cylindrical spool 110 or to detect the initial presence of the coiled tubing string 130 in the nonmagnetic cylindrical spool 110. The control panel may also evaluate the reading of the synchronization sensor 31 and determine whether a maximum magnetic flux value is at that time being detected and may then in turn notify the sensors 30 of such reading.

Even though the above disclosure describes identifying the location of tool joints 90 in a tubing string 95 and identifying the presence of a coiled tubing string 130 in the nonmagnetic cylindrical spool 110, the present invention is expressly not limited to such applications, and may be useful in various other applications. The present invention would prove useful, for example, for identifying the initial presence of a tubing string 95 in a BOP spool or another predetermined section of pipe. For instance, the computer 51 or control panel may also give an audio and/or visual signal to the operator signifying the initial presence of the tubing string 95 in the predetermined section of pipe and also when the last of the tubing string 95 exits the predetermined section of pipe. The present invention is further not limited to use in a well bore. It will be appreciated that the invention may detect changes in mass and/or diameter of ferrous objects passing through a cylindrical space in any technology or application calling for such functionality.

Although the present invention and its advantages have been described in detail, it should be understood that various changes, substitutions and alterations can be made herein without departing from the spirit and scope of the invention as defined by the appended claims.

We claim:

1. A method for detecting ferrous changes passing axially through a cylindrical space, the method comprising:
    (A) surrounding the cylindrical space with a nonmagnetic cylinder having an outer wall and a cylindrical axis;
    (B) creating an alternating magnetic field in the cylindrical space, the magnetic field created by positioning a rotatable permanent magnet proximate the outer wall;
    (C) monitoring the magnetic field with magnetic flux sensors placed outside the outer wall; and
    (D) responsive to said monitoring in (C), detecting changes in the magnetic field as ferrous matter passes axially through the cylindrical space.

2. The method of claim 1, further comprising:
    (E) recognizing changes in the magnetic field as a specific ferrous change by reference to predetermined changes in the magnetic field expected for said specific ferrous change.

3. The method of claim 2, wherein (E) is accomplished by at least one technique selected from the group consisting of:
    (1) threshold detection; and
    (2) waveform detection.

4. The method of claim 1, in which the rotatable permanent magnet rotates about a predetermined axis, the predetermined axis oriented in an attitude selected from the group consisting of:
    (1) parallel to the cylindrical axis; and
    (2) orthogonal to the cylindrical axis.

5. An apparatus for identifying ferrous changes as a tool joint in a jointed tubing string, the tubing string moving in and out of a well bore, a plurality of the tool joints connecting sections of the jointed tubing string, the apparatus comprising:
    a nonmagnetic cylindrical spool having a cylindrical axis, the tubing string and tool joints disposed to move axially in or out of the nonmagnetic cylindrical spool; and
    a sensor device attached to the nonmagnetic cylindrical spool, the sensor device having a source piece operable to be in magnetic flux communication with at least one sensor piece, the source piece comprising a permanent magnet, the permanent magnet being operatively rotatable.

6. The apparatus of claim 5, wherein the source piece further comprises a motor and a source field shaper.

7. The apparatus of claim 6, wherein the motor rotates the permanent magnet.

8. The apparatus of claim 6, wherein the motor is selected from the group consisting of:
   (1) an electric motor; and
   (2) a pneumatic motor.

9. The apparatus of claim 5, wherein the sensor piece includes at least one sensor and a sensor field shaper.

10. The apparatus of claim 9, wherein sensors included in the sensor piece are selected from the group consisting of:
    (1) Hall effect sensors;
    (2) Giant Magnetoresistive sensors; and
    (3) Anisotropic Magnetoresistive sensors.

11. The apparatus of claim 5, wherein the source piece opposes the sensor piece substantially diametrically across the nonmagnetic cylindrical spool.

12. The apparatus of claim 5, wherein rotation of the permanent magnet creates an alternating magnetic field within the nonmagnetic cylindrical spool, the magnetic field having alternating high and low flux values, the sensor piece disposed to recognize changes in at least the high flux values as the tubing string and tool joints move axially in and out of the nonmagnetic cylindrical spool.

13. The apparatus of claim 12, further comprising a synchronization sensor, the synchronization sensor disposed to prompt the sensor piece to sample the magnetic field upon detection by the synchronization sensor of high flux values.

14. The apparatus of claim 12, further comprising circuitry, the circuitry disposed to process said recognized changes in the magnetic field so as to differentiate when tubing string and tool joints are passing through the magnetic field.

15. The apparatus of claim 14, in which the circuitry processes said recognized changes using at least one technique from the group consisting of:
    (1) threshold detection; and
    (2) waveform detection.

16. The apparatus of claim 5, wherein the permanent magnet is disposed to rotate about a predetermined axis, the predetermined axis oriented in an attitude selected from the group consisting of:
    (1) parallel to the cylindrical axis; and
    (2) orthogonal to the cylindrical axis.

17. A method of identifying ferrous changes as a plurality of the tool joints connecting a jointed tubing string move in and out of a well bore, the method comprising:
    (A) moving a tubing string in or out of a well bore;
    (B) causing the tubing string to pass through a nonmagnetic cylindrical spool;
    (C) creating an alternating magnetic field across the nonmagnetic cylindrical spool;
    (D) sensing a deviation in the alternating magnetic field; and
    (E) identifying the deviation in the alternating magnetic field as the presence of a ferrous change within the nonmagnetic cylindrical spool, the ferrous change indicative of the presence within the nonmagnetic cylindrical spool of a tool joint on the tubing string.

18. The method of claim 17, wherein (C) further comprises directing the alternating magnetic field.

19. The method of claim 17, wherein (C) further comprises rotating a permanent magnet.

20. The method of claim 19, in which the rotating permanent magnet rotates about a predetermined axis, the predetermined axis oriented in an attitude selected from the group consisting of:
    (1) parallel to the cylindrical axis of the nonmagnetic cylindrical spool; and
    (2) orthogonal to the cylindrical axis of the nonmagnetic cylindrical spool.

21. The method of claim 19, wherein rotating the permanent magnet further comprises rotating the permanent magnet with a motor.

22. The method of claim 21, wherein the motor is selected from the group consisting of:
    (1) a pneumatic motor; and
    (2) an electric motor.

23. The method of claim 21, wherein the permanent magnet and motor are secured to the nonmagnetic cylindrical spool.

24. The method of claim 17, wherein the alternating magnetic field comprises alternating high and low flux values, and wherein (D) further comprises disposing a first sensor to identify at least high flux values, and responsive to such identification, causing the first sensor to prompt a second sensor to sample the magnetic field.

25. The method of claim 17, wherein (D) further comprises reducing external magnetic interference via shielding.

26. The method of claim 17, wherein (E) further comprises identifying the deviation as an event selected from the group consisting of:
    (1) the presence of a tool joint in the nonmagnetic cylindrical spool;
    (2) the presence of a tube in the tubing string in the nonmagnetic cylindrical spool;
    (3) an entry of the tubing string into the nonmagnetic cylindrical spool; and
    (4) an exit of the tubing string from the nonmagnetic cylindrical spool.

27. The method of claim 17, wherein (E) is accomplished by at least one technique selected from the group consisting of:
    (1) threshold detection; and
    (2) waveform detection.

28. A method of identifying ferrous changes while moving a jointed tubing string in and out of a well bore, a plurality of tool joints connecting the jointed tubing string, the method comprising:
    (A) moving the tubing string through an upper BOP, a lower BOP, and a nonmagnetic cylindrical spool;
    (B) separating the upper BOP and the lower BOP with the nonmagnetic cylindrical spool;
    (C) creating an alternating magnetic field across the nonmagnetic cylindrical spool;
    (D) sensing a deviation in the alternating magnetic field;
    (E) identifying the deviation in the alternating magnetic field as the presence of ferrous change within the nonmagnetic cylindrical spool, the ferrous change indicative of the presence within the nonmagnetic cylindrical spool of a tool joint on the tubing string; and
    (F) moving the tubing string in or out of the well bore without the tool joint contacting the upper BOP and the lower BOP.

29. The method of claim 28, wherein (C) further comprises directing the alternating magnetic field.

30. The method of claim 28, wherein (C) further comprises rotating a permanent magnet.

31. The method of claim 30, in which the rotating permanent magnet rotates about a predetermined axis, the predetermined axis oriented in an attitude selected from the group consisting of:
- (1) parallel to the cylindrical axis of the nonmagnetic cylindrical spool; and
- (2) orthogonal to the cylindrical axis of the nonmagnetic cylindrical spool.

32. The method of claim 30, wherein rotating the permanent magnet further comprises rotating the permanent magnet with a motor.

33. The method of claim 32, wherein the motor is selected from the group consisting of:
- (1) a pneumatic motor; and
- (2) an electric motor.

34. The method of claim 32, wherein the permanent magnet and motor are secured to the nonmagnetic cylindrical spool.

35. The method of claim 28, wherein the alternating magnetic field comprises alternating high and low flux values, and wherein (D) further comprises disposing a first sensor to identify at least high flux values, and responsive to such identification, causing the first sensor to prompt a second sensor to sample the magnetic field.

36. The method of claim 28, wherein (D) further comprises reducing external magnetic interference via shielding.

37. The method of claim 28, wherein (E) further comprises identifying the deviation as an event selected from the group consisting of:
- (1) the presence of a tool joint in the nonmagnetic cylindrical spool;
- (2) the presence of a tube in the tubing string in the nonmagnetic cylindrical spool;
- (3) an entry of the tubing string into the nonmagnetic cylindrical spool; and
- (4) an exit of the tubing string from the nonmagnetic cylindrical spool.

38. The method of claim 28, wherein (F) further comprises isolating the pressure below the lower BOP from the pressure above the upper BOP.

39. The method of claim 28, wherein (E) is accomplished by at least one technique selected from the group consisting of:
- (1) threshold detection; and
- (2) waveform detection.

40. An apparatus for identifying ferrous changes in a jointed tubing string, a plurality of tool joints connecting the jointed tubing string, the tubing string moving in and out of a well bore, the apparatus comprising:
- a nonmagnetic cylindrical spool, an upper BOP, and a lower BOP, the tubing string moving in or out of the well bore through the nonmagnetic cylindrical spool, the upper BOP, and the lower BOP;
- the nonmagnetic cylindrical spool separating the upper BOP and the lower BOP;
- the upper BOP closable around the tubing string to form a pressure lock;
- the lower BOP closable around the tubing string to form a pressure lock;
- a rotatable permanent magnet attached to the nonmagnetic cylindrical spool, the permanent magnet rotatable about an axis substantially orthogonal to the cylindrical axis of the nonmagnetic cylindrical spool;
- a motor secured to the nonmagnetic cylindrical spool, the motor disposed to rotate the permanent magnet;
- a source field shaper secured to the nonmagnetic cylindrical spool, the source field shaper disposed to shape the magnetic field created by the rotating permanent magnet;
- at least two sensors secured to the nonmagnetic cylindrical spool, the sensors disposed to identify changes in the magnetic field;
- the sensors further disposed to create a processor-readable signal whose signature corresponds to changes in the magnetic field;
- at least one sensor field shaper attached to the nonmagnetic cylindrical spool, the sensor field shaper disposed to shield the sensors from external magnetic interference;
- the upper BOP openable to allow passage of the tool joint; and
- the lower BOP openable to allow passage of the tool joint.

41. The apparatus of claim 40, the sensors disposed to identify the changes in the magnetic field as an event selected from the group consisting of:
- (1) the presence of a tool joint in the nonmagnetic cylindrical spool;
- (2) the presence of a tube in the tubing string in the nonmagnetic cylindrical spool;
- (3) an entry of the tubing string into the nonmagnetic cylindrical spool; and
- (4) an exit of the tubing string from the nonmagnetic cylindrical spool.

42. The apparatus of claim 40, wherein the rotatable permanent magnet and source field shaper oppose the sensors and sensor field shaper substantially diametrically across the nonmagnetic cylindrical spool.

43. The apparatus of claim 40, wherein rotation of the permanent magnet creates an alternating magnetic field within the nonmagnetic cylindrical spool, the magnetic field having alternating high and low flux values, the sensors disposed to recognize changes in at least the high flux values as the tubing string and tool joints move axially in and out of the nonmagnetic cylindrical spool.

44. The apparatus of claim 43, further comprising a synchronization sensor, the synchronization sensor disposed to prompt the sensors to sample the magnetic field upon detection by the synchronization sensor of high flux values.

45. The apparatus of claim 40, further comprising circuitry, the circuitry disposed to process said recognized changes in the magnetic field so as to differentiate when tubing string and tool joints are passing through the magnetic field.

46. The apparatus of claim 45, in which the circuitry processes said recognized changes using at least one technique from the group consisting of:
- (1) threshold detection; and
- (2) waveform detection.

47. The apparatus of claim 40, wherein ones of the sensors are selected from the group consisting of:
- (1) a Hall effect sensor;
- (2) a Giant Magnetoresistive sensor; and
- (3) an Anisotropic Magnetoresistive sensor.

48. The apparatus of claim 40, wherein the motor is selected from the group consisting of:
- (1) an electric motor; and
- (2) a pneumatic motor.

49. An apparatus for identifying ferrous changes as a coiled tubing string moves in and out of a well bore, the apparatus comprising:
- a nonmagnetic cylindrical spool having a cylindrical axis, the coiled tubing string disposed to move in and out of the nonmagnetic cylindrical spool along the cylindrical axis; and a sensor device attached to the nonmagnetic cylindrical spool, the sensor device having a source piece operable to be in magnetic flux communication with at least one sensor piece, the source piece comprising a permanent magnet, the permanent magnet being operatively rotatable.

50. The apparatus of claim 49, wherein the source piece further comprises a motor and a source field shaper.

51. The apparatus of claim 50, wherein the motor rotates the permanent magnet.

52. The apparatus of claim 50, wherein the motor is selected from the group consisting of:
  (1) an electric motor; and
  (2) a pneumatic motor.

53. The apparatus of claim 49, wherein the sensor piece includes at least one sensor and a sensor field shaper.

54. The apparatus of claim 53, wherein sensors included in the sensor piece are selected from the group consisting of:
  (1) Hall effect sensors;
  (2) Giant Magnetoresistive sensors; and
  (3) Anisotropic Magnetoresistive sensors.

55. The apparatus of claim 49, wherein the source piece opposes the sensor piece substantially diametrically across the nonmagnetic cylindrical spool.

56. The apparatus of claim 49, wherein rotation of the permanent magnet creates an alternating magnetic field within the nonmagnetic cylindrical spool, the magnetic field having alternating high and low flux values, the sensor piece disposed to recognize changes in at least the high flux values as the coiled tubing string moves axially in and out of the nonmagnetic cylindrical spool.

57. The apparatus of claim 56, further comprising a synchronization sensor, the synchronization sensor disposed to prompt the sensor piece to sample the magnetic field upon detection by the synchronization sensor of high flux values.

58. The apparatus of claim 56, further comprising circuitry, the circuitry disposed to process said recognized changes in the magnetic field so as to differentiate when the coiled tubing string is present and absent in the nonmagnetic cylindrical spool.

59. The apparatus of claim 58, in which the circuitry processes said recognized changes using at least one technique from the group consisting of:
  (1) threshold detection; and
  (2) waveform detection.

60. The apparatus of claim 49, wherein the permanent magnet is disposed to rotate about a predetermined axis, the predetermined axis oriented in an attitude selected from the group consisting of:
  (1) parallel to the cylindrical axis; and
  (2) orthogonal to the cylindrical axis.

61. A method of identifying ferrous changes as a coiled tubing string moves in and out of a well bore, the method comprising:
  (A) moving a coiled tubing string in and out of a well bore;
  (B) causing the coiled tubing string to pass through a nonmagnetic cylindrical spool;
  (C) creating an alternating magnetic field across the nonmagnetic cylindrical spool;
  (D) sensing a deviation in the alternating magnetic field; and
  (E) identifying the deviation in the alternating magnetic field as the presence of a ferrous change within the nonmagnetic cylindrical spool, the ferrous change indicative of the presence within the nonmagnetic cylindrical spool of the coiled tubing string.

62. The method of claim 61, wherein (C) further comprises directing the alternating magnetic field.

63. The method of claim 61, wherein (C) further comprises rotating a permanent magnet.

64. The method of claim 63, in which the rotating permanent magnet rotates about a predetermined axis, the predetermined axis oriented in an attitude selected from the group consisting of:
  (1) parallel to the cylindrical axis of the nonmagnetic cylindrical spool; and
  (2) orthogonal to the cylindrical axis of the nonmagnetic cylindrical spool.

65. The method of claim 63, wherein rotating the permanent magnet further comprises rotating the permanent magnet with a motor.

66. The method of claim 65, wherein the motor is selected from the group consisting of:
  (1) a pneumatic motor; and
  (2) an electric motor.

67. The method of claim 65, wherein the permanent magnet and motor are secured to the nonmagnetic cylindrical spool.

68. The method of claim 61, wherein the alternating magnetic field comprises alternating high and low flux values, and wherein (D) further comprises disposing a first sensor to identify at least high flux values, and responsive to such identification, causing the first sensor to prompt a second sensor to sample the magnetic field.

69. The method of claim 61, wherein (D) further comprises reducing external magnetic interference via shielding.

70. The method of claim 61, wherein (E) further comprises identifying the deviation as an event selected from the group consisting of:
  (1) the presence of the coiled tubing string in the nonmagnetic cylindrical spool;
  (2) an entry of the coiled tubing string into the nonmagnetic cylindrical spool; and
  (3) an exit of the coiled tubing string from the nonmagnetic cylindrical spool.

71. The method of claim 61, wherein (E) is accomplished by at least one technique selected from the group consisting of:
  (1) threshold detection; and
  (2) waveform detection.

* * * * *

UNITED STATES PATENT AND TRADEMARK OFFICE
CERTIFICATE OF CORRECTION

PATENT NO.    : 6,720,764 B2
DATED         : April 16, 2002
INVENTOR(S)   : Mahendran Relton et al.

It is certified that error appears in the above-identified patent and that said Letters Patent is hereby corrected as shown below:

Drawings,
Replace the following figures 1, 3, 5-6 and 9-12.

Signed and Sealed this

Sixth Day of July, 2004

JON W. DUDAS
*Acting Director of the United States Patent and Trademark Office*